(12) United States Patent
Villarete et al.

(10) Patent No.: US 7,232,563 B2
(45) Date of Patent: Jun. 19, 2007

(54) HYBRID INTERFERON/INTERFERON TAU PROTEINS, COMPOSITIONS AND METHODS OF USE

(75) Inventors: Lorelie H. Villarete, Alameda, CA (US); Jackeline Campos, Pittsburg, CA (US); Wayne Li, Poway, CA (US)

(73) Assignee: Pepgen Corporation, Alameda, CA (US)

( * ) Notice: Subject to any disclaimer, the term of this patent is extended or adjusted under 35 U.S.C. 154(b) by 669 days.

(21) Appl. No.: 10/218,338

(22) Filed: Aug. 12, 2002

(65) Prior Publication Data

US 2003/0130486 A1    Jul. 10, 2003

Related U.S. Application Data

(60) Provisional application No. 60/311,866, filed on Aug. 12, 2001.

(51) Int. Cl.
*A61K 38/21* (2006.01)
*A61K 39/00* (2006.01)
*C07K 14/00* (2006.01)

(52) U.S. Cl. .................. 424/85.7; 424/185.1; 530/351

(58) Field of Classification Search ..................... None
See application file for complete search history.

(56) References Cited

U.S. PATENT DOCUMENTS

| | | | |
|---|---|---|---|
| 4,276,282 A | 6/1981 | Sugimoto et al. | |
| 4,414,150 A | 11/1983 | Goeddel | |
| 4,456,784 A | 6/1984 | Goeddel | |
| 4,460,574 A | 7/1984 | Yabrov | |
| 4,507,281 A | 3/1985 | Asculai et al. | |
| 4,569,908 A | 2/1986 | Mark et al. | |
| 4,636,383 A | 1/1987 | Nagabhushan et al. | |
| 4,758,428 A | 7/1988 | Mark et al. | |
| 4,846,782 A | 7/1989 | Bonnem | |
| 4,874,609 A | 10/1989 | Rideout et al. | |
| 4,892,743 A | 1/1990 | Leibowitz et al. | |
| 4,897,471 A | 1/1990 | Stabinsky | |

(Continued)

FOREIGN PATENT DOCUMENTS

EP     0 146 903 A2    7/1985

(Continued)

OTHER PUBLICATIONS

Ngo et al., 1994, The Protein Folding Problem and Tertiary Structure Prediction, pp. 492-495.*
Wells, Aditivity of Mutational Effects in Proteins, 1990, Biochemistry, vol. 26, No. 37, pp. 8509-8517.*
Bazer, F.W., and Johnson, H.M., "Type I Conceptus Interferons: Maternal Recognition of Pregnancy Signal and Potential Therapeutic Agents", *American J. of Reproductive Immun.* 26:19-22 (1991).
Bazer, F.W., et al., "Roles of Conceptus Secretory products in Establishment of Pregnancy," *J. Reprod. Fert.* 76:841-850.

(Continued)

*Primary Examiner*—Christine J. Saoud
*Assistant Examiner*—Jegatheesan Seharaseyon
(74) *Attorney, Agent, or Firm*—Brian S. Boyer; Perkins Coie LLP

(57) ABSTRACT

The present invention relates to hybrid interferon fusion proteins formed of an interferon-α protein where the C-terminal region of the interferon-α protein is replaced by a C-terminal region of interferon-τ. Also described are nucleic acid sequences encoding the interferon fusion proteins, expression vectors containing such sequences, and therapeutic applications of the interferon fusion proteins. The therapeutic applications include antiviral, anticellular proliferation, and anti-inflammatory applications. One advantage of the interferon fusion polypeptides of the present invention is that they have lower cytotoxic side effects when used to treat cells.

8 Claims, 13 Drawing Sheets

List of oligos synthesized:

| | | |
|---|---|---|
| HVV1F1T1 | PCTAGGCTCGAGAA | SEQ ID NO:3 |
| HVV1F1T2 | PGAGATGTGATTTGCCAGAGACTCACTCTT | SEQ ID NO:4 |
| HVV1F1T3 | PTGGACAACAGAAGAACTTTGATGCTTTT | SEQ ID NO:5 |
| HVV1F1T4 | PGGCCCAAATGTCTAGAATCTCTCCATCCTC | SEQ ID NO:6 |
| HVV1F1T5 | PTTGTTTGATGGATAGACACGATTTCGGTTT | SEQ ID NO:7 |
| HVV1F1T6 | PCCCACAAGAAGAATTCCCTGCTCGCG | SEQ ID NO:8 |
| HVV1F1B1 | PGATCCGCGAGCA | SEQ ID NO:9 |
| HVV1F1B2 | PGGGAATTCTTCTTGTGGGAAACCGAAATCGT | SEQ ID NO:10 |
| HVV1F1B3 | PGTCTATCCATCAAACAAGAGGATGGAGA | SEQ ID NO:11 |
| HVV1F1B4 | PGATTCTAGACATTTGGGCCAAAAGCATCA | SEQ ID NO:12 |
| HVV1F1B5 | PAAGTTCTTCTGTTGTCCAAAGAGTGAGTCT | SEQ ID NO:13 |
| HVV1F1B6 | PCTGGCAAATCACATCTCTTCTCGAGC | SEQ ID NO:14 |

Final ligated product (SEQ ID NO:15)

```
      [ HVV1F1T1 ][ HVV1F1T2           ][ HVV1F1T3
5'-CTAGGCTCGAGAAGATGTGATTTGCCAGAGACTCACTCTTTGGACAACAGAAGAACTTTGATGCT
3'-CGAGCTCTTCTCTACACTAAACGGTCTCTGAGTGAGAAACCTGTTGTCTTCTTGAAACTACGA
     [ HVV1F1B6           ][ HVV1F1B5          ][ HVV1

][ HVV1F1T4              ][ HVV1F1T5            ][ HVV1F
TTTGCCCAAATGTCTAGAATCTCTCCATCCTCTTGTTTGATGGATAGACACGATTTCGGTTTCCCACAA
AAACCGGGTTTACAGATCTTAGAGAGGTAGGAGAACAAACTACCTATCTGTGCTAAAGCCAAAGGGTGTT
F1B4                 ][ HVV1F1B3              ][ HVV1F1B2

1T6         ]
GAAGAATTCCCTGCTCGCG-3'
CTTCTTAAGGGACGAGCGCCTAG-5'
          ][ HVV1F1B1]
```

U.S. PATENT DOCUMENTS

| | | | |
|---|---|---|---|
| 4,917,887 | A | 4/1990 | Hauptmann et al. |
| 4,997,646 | A | 3/1991 | Hansen et al. |
| 5,019,382 | A | 5/1991 | Cummins, Jr. |
| 5,705,363 | A | 1/1998 | Imakawa |
| 5,738,845 | A | 4/1998 | Imakawa |
| 5,939,286 | A | 8/1999 | Johnson et al. |
| 5,958,402 | A | 9/1999 | Bazer et al. |
| 6,174,996 | B1 | 1/2001 | Johnson et al. |

FOREIGN PATENT DOCUMENTS

| | | |
|---|---|---|
| EP | 0 367 063 | 5/1990 |
| WO | WO 83/02461 | 7/1983 |
| WO | WO 90/09806 | 9/1990 |
| WO | WO 93/12146 | 12/1992 |
| WO | WO 94/10113 | 5/1994 |
| WO | WO 94/10313 | 5/1994 |
| WO | WO 97/33998 | 9/1997 |
| WO | WO 99/20653 A | 4/1999 |

OTHER PUBLICATIONS

Bazer, F.W., et al., "Roles of Ovine Trophoblast Protein-1 and Oestradiol/Prolactin in the Establishment of Pregnancy in Sheep and Pigs", *Reprod. Fertil. Dev.* 4:335-340 (1992).

Bonnem, E.M., and Spiegel, R.J., "Interferon-α: Current Status and Future promise," *J. Biological Response Modifiers* 3:580-598 (1984).

Charpigny, G., et al. (1988) *FEBS Lett.* 228:12-16.

Farin, C.E. et al., "Expression of Trophoblastic Interferon Genes in Sheep and Cattle", *Biol. of Reprod.* 43:210-218 (1990).

Godkin, et al., "Proteins Release by Cultured Day 15-16 Conceptuses Prolong Luteal Maintenance When Introduced into the Uterine Lumen of Cyclic Ewes," *J. Reprod. Fertil.* 71:57-64 (1984).

Hansen, T.R., et al., "Complex Binding of the Embryonic Interferon, Ovine Trophoblast protein-1, to Endometrial Receptors", *J. Interferon Res.* 9:215-225 (1989).

Hansen, T.R., et al., "The Gene for Trophoblast Interferons and the Related Interferon-α11 Possess Distinct 5' promoter and 3'-Flanking Sequence", *J. Biol. Chem.* 266(5):3060-3067 (1991).

Imakawa, K., et al., "Interferon-like sequence of ovine trophoblast protein secreted by embryonic trophectoderm", Nature 330:377-379 (1987).

Imakawa, K., et al., "Molecular Cloning and Characterization of Complementary Deoxyribonucleic Acids Corresponding to Bovine Trophoblast protein 1: A Comparison with Ovine Trophoblast Protein-1 and Bovine Interferon-α11", *Mol. Endocrin.* 3(1):127-139 (1989).

Jarpe, M.A., et al., "Predicted Structural Motif of IFN τ," *Prot. Engin.* 7(7):863-867 (1994).

Leaman, D.W., et al. "Genes for Trophoblast Interferons and their Distribution among Mammals", *Reprod. Fertil. Dev.* 4:349-353 (1992).

Leaman, D.W., and Roberts, R.M., "Genes for the Trophoblast Interferons in Sheep, Goat, and Musk Ox and Distribution of Related Genes Among Mammals", *J. Interferon Res.* 12;1-11 (1992).

Li, J., and Roberts, R.M., "Structure-Function Relationships in the Interferon-τ (IFN-τ): changes in Receptor binding and in Antiviral and Antiproliferative Activities Resulting from Site-Directed Multagenesis Performed Near the Carboxyl Terminus," *J. Biol. Chem* 269(40):248246-24833 (1994).

Newton, G.R., et al., "Inhibition of Lymphocyte Proliferation by Ovine Trophoblast Protein-1 and a High Molecular Weight Glycoprotein Produced by the Peri-Implantation Sheep Conceptus", *Am. J. Reprod. Immunol.* 19:99-107 (1989).

Oldham, R.K. "Biologicals for Cancer Treatment: Interferons," *Hosp. Pract.* Dec. 15. pp. 71-86 (1985).

Ott, T.L., et al., "Cloning and Expression in *Saccharomyces cerevisiae* of a Synthetic Gene for the Type-I Trophoblast Interferon Ovine Trophoblast protein-1: Purification and Antiviral Activity", *J. Interferon Res.* 11:357-364 (1991).

Pontzer, C.H., et al., "Antiviral Activity of the Pregnancy Recognition Hormone Ovine Trophoblast Protein-1", *Biochem. and Biophys. Res. Commun.* 152(2):801-807 (1988).

Pontzer, C.H., et al., "Localization of an antiviral site on the pregnancy recognition hormone, ovine trophoblast protein-1", *Proc. Natl. Acad. Sci. USA* 87:5945-5949 (1990).

Pontzer, C.H., et al., "Antiproliferative Acticity of a Pregnancy Recognition Hormone, Ovine Trophoblast Protein-1", *Cancer Res.* 51:5304-5307 (1991).

Pontzer, C.H., et al., "Structure/Function Studies with Interferon Tau:Evidence for Multiple Active Site," *J. Interferon Res.* 14:133-141 (1994).

Quesada, J.R., et al., "Alpha Interferon for Induction of Remission in Hairy-Cell Leukemia," *N. Engl. J. Med.* 310:15-18 (1984).

Roberts, R.M., et al., "Interferons at the placenta interface", *J. Reprod. Fert.*, Suppl. 41:63-74 (1990).

Roberts, R.M., et al., "Unique Features of the Trophoblast Interferons", *Pharmac.Ther.* 51:329-345 (1991a).

Roberts, R.M., et al., "The Polypeptides and genes for ovine and bovine trophoblast protein-1", *J. Reprod. Fert.*, Suppl. 43:-3-12 (1991b).

Roberts, R.M., et al., "Interferons as Hormones of Pregnancy", *Endocrine Rev.* 13(3):432-452 (1992).

Salamonsen, L.A., et al., "Interferon-Alpha Mimics Effects of Ovine Trophoblast Protein 1 on Prostaglandin and Protein Secretion by Ovine Endometrial Cells in Vitro," *J. Endocrin.* 117:R1-R04 (1988).

Stewart, H.J., et al. "Interferon Sequence Homology and Receptor Binding Activity of Ovine Trophoblast Antileuteolytic Protein," *J. Endicrinol.* 115:R13-15 (1987).

Subramaniam, P.S., et al., "Differential Recognition of the Type I Interferon Receptor by Interferons τ and α is Responsible for Their Disparate Cytotoxicities," *Proc. Natl. Acad. Sci. USA* 92:12270-12274 (1995).

Subramaniam, P.S., and Johnson, H.M., "Differential Recognition of the Type I Receptor by the Type I Interferons, IFN τ and IFNα is Responsible for Their Differential Cytotoxicities," *FASEB J.* 9(4):A1021 Abstract (1995).

Tuo, W., et al., "Natural Killer Cell Activity of Lymphocytes Exposed to Ovine, Type I, Trophoblast Interferon", *AJRI* 29:26-34(1993).

Vallet, J.L., et al., "The Effect of Ovine Trophoblast Protein0One on Endometrial Protein Secretion and Cyclic Nucleotides", *Biol. Reprod.* 37:1307-1316 (1987).

Vallet, J.L., et al., "Effect of ovine conceptus secretory proteins and purified ovine trophoblast protein-1 on interoestrous interval and plasma concentrations of prostaglandins F-2α and E and 13, 14-dihydro-15-keto-prostaglandin F-2α in cyclic ewes", *J. Reprod. Fert.* 84:493-504 (1988).

Whaley, A.E., et al., "Molecular Cloning of Unique Interferons from Human Placenta," In *Society of Reproduction, 24th Annual Meeting*, p. 186 (1991).

Whaley, A.E., et al., (1994) *J. Biol. Chem.* 269: 10864-68.

White, et al., in *Principles of Biochemistry*, McGraw-Hill, New York, NY, 6th Edition, pp. 860-874 (1978).

Wilson, M.E., et al., "Proteins of Ovine Blastocyst Origin," *Biol. Reproduct.* 20 (Sup 1):101A Abstract (1979).

Yong, Ki, et al., "Insulin-Like Growth Factors in Sheep Uterine Fluids: Concentrations and Relationship to Ovine Trophoblast Protein-1 production during Early pregnancy", *Biol. Reprod.* 45: 135-142 (1991).

International Search Report, PCT/US02/25691, Int'l. Filing Date: Aug. 12, 2002.

Horisberger, M.A., et al., "Interferon-Alpha Hybrids," *Pharmac. Ther.*, 66:3 507-534 (1995).

Database EMBL "Human Interferon-Alpha I" XP 002344928, EBI Database Accession No. AAW43380, (Apr. 7, 1998).

\* cited by examiner

List of oligos synthesized:

```
HVV1F1T1   PCTAGGCTCGAGAA                        SEQ ID NO:3
HVV1F1T2   PGAGATGTGATTTGCCAGAGACTCACTCTT        SEQ ID NO:4
HVV1F1T3   PTGGACAACAGAAGAACTTTGATGCTTTT         SEQ ID NO:5
HVV1F1T4   PGGCCCAAATGTCTAGAATCTCTCCATCCTC       SEQ ID NO:6
HVV1F1T5   PTTGTTTGATGGATAGACACGATTTCGGTTT       SEQ ID NO:7
HVV1F1T6   PCCCACAAGAAGAATTCCCTGCTCGCG           SEQ ID NO:8
HVV1F1B1   PGATCCGCGAGCA                         SEQ ID NO:9
HVV1F1B2   PGGGAATTCTTCTTGTGGGAAACCGAAATCGT      SEQ ID NO:10
HVV1F1B3   PGTCTATCCATCAAACAAGAGGATGGAGA         SEQ ID NO:11
HVV1F1B4   PGATTCTAGACATTTGGGCCAAAAGCATCA        SEQ ID NO:12
HVV1F1B5   PAAGTTCTTCTGTTGTCCAAAGAGTGAGTCT       SEQ ID NO:13
HVV1F1B6   PCTGGCAAATCACATCTCTTCTCGAGC           SEQ ID NO:14
```

Final ligated product (SEQ ID NO:15)

```
      [  HVV1F1T1  ][  HVV1F1T2           ][  HVV1F1T3
5'-CTAGGCTCGAGAAGAGATGTGATTTGCCAGAGACTCACTCTTTGGACAACAGAAGAACTTTGATGCT
   3'-CGAGCTCTTCTCTACACTAAACGGTCTCTGAGTGAGAAACCTGTTGTCTTCTTGAAACTACGA
       [   HVV1F1B6         ][   HVV1F1B5          ][   HVV1

][  HVV1F1T4             ][  HVV1F1T5             ][  HVV1F
TTTGGCCCAAATGTCTAGAATCTCTCCATCCTCTTGTTTGATGGATAGACACGATTTCGGTTTCCCACAA
AAACCGGGTTTACAGATCTTAGAGAGGTAGGAGAACAAACTACCTATCTGTGCTAAAGCCAAAGGGTGTT
F1B4             ][   HVV1F1B3        ][   HVV1F1B2

1T6               ]
GAAGAATTCCCTGCTCGCG-3'
CTTCTTAAGGGACGAGCGCCTAG-5'
       ][  HVV1F1B1]
```

Fig. 1

List of oligos synthesized:

| | | |
|---|---|---|
| HVV1F2T1 | PAATTTGACGGTAAC | SEQ ID NO:16 |
| HVV1F2T2 | PCAATTCCAAAAGGCTCCTGCTATTTCTGT | SEQ ID NO:17 |
| HVV1F2T3 | PTTTGCACGAGTTGATTCAACAAATTT | SEQ ID NO:18 |
| HVV1F2T4 | PTCAACTTGTTCACCACTAAGGACTCTT | SEQ ID NO:19 |
| HVV1F2T5 | PCTGCTGCCTGGGACGAAGACTTGTTGGAC | SEQ ID NO:20 |
| HVV1F2T6 | PAAGTTCTGTACTGAGCTCAGCGCGAATG | SEQ ID NO:21 |
| HVV1F2B1 | PGATCCATTCGCGCT | SEQ ID NO:22 |
| HVV1F2B2 | PGAGCTCAGTACAGAACTTGTCCAACAA | SEQ ID NO:23 |
| HVV1F2B3 | PGTCTTCGTCCCAGGCAGCAGAAGAGTCCT | SEQ ID NO:24 |
| HVV1F2B4 | PTAGTGGTGAACAAGTTGAAAATTTGTTG | SEQ ID NO:25 |
| HVV1F2B5 | PAATCAACTCGTGCAAAACAGAAATA | SEQ ID NO:26 |
| HVV1F2B6 | PGCAGGAGCCTTTTGGAATTGGTTACCGTCA | SEQ ID NO:27 |

Final ligated product: (SEQ ID NO:28)

```
     [ HVV1F2T1   ][ HVV1F2T2             ][ HVV1F2T3
5'-AATTTGACGGTAACCAATTCCAAAAGGCTCCTGCTATTTCTGTTTTGCACGAGTTGATTCAACAAAT
   3'-ACTGCCATTGGTTAAGGTTTTCCGAGGACGATAAAGACAAAACGTGCTCAACTAAGTTGTTTA
     [ HVV1F2B6             ][ HVV1F2B5            ][ HVV1F

][ HVV1F2T4            ][ HVV1F2T5             ][ HVV1F2T6
TTTCAACTTGTTCACCACTAAGGACTCTTCTGCTGCCTGGGACGAAGACTTGTTGGACAAGTTCTGTACT
AAAGTTGAACAAGTGGTGATTCCTGAGAAGACGACGGACCCTGCTTCTGAACAACCTGTTCAAGACATGA
2B4           ][ HVV1F2B3           ][ HVV1F2B2

]
GAGCTCAGCGCGAATG-3'
CTCGAGTCGCGCTTACCTAG-5'
     ][ HVV1F2B1 ]
```

Fig. 2

List of oligos synthesized:

| | | | |
|---|---|---|---|
| HVV1F3T1 | PTTACCAACAATT | SEQ ID NO:29 |
| HVV1F3T2 | PGAACGACTTGGAGGCTTGTGTTATGC | SEQ ID NO:30 |
| HVV1F3T3 | PAAGAGGAGAGAGTCGGTGAGACCCCATTGATG | SEQ ID NO:31 |
| HVV1F3T4 | PAACGCTGATTCCATCTTGGCTGTCAAGAAGT | SEQ ID NO:32 |
| HVV1F3T5 | PACTTCAGAAGAATTCAGCTCATTTG | SEQ ID NO:33 |
| HVV1F3B1 | PGATCCAAATGAGC | SEQ ID NO:34 |
| HVV1F3B2 | PTGAATTCTTCTGAAGTACTTCTTGACAGCCAA | SEQ ID NO:35 |
| HVV1F3B3 | PGATGGAATCAGCGTTCATCAATGGGGT | SEQ ID NO:36 |
| HVV1F3B4 | PCTCACCGACTCTCTCCTCTTGCATAACACA | SEQ ID NO:37 |
| HVV1F3B5 | PAGCCTCCAAGTCGTTCAATTGTTGGTAAAGCT | SEQ ID NO:38 |

Final ligated product (SEQ ID NO:39)

```
         [ HVV1F3T1 ] [ HVV1F3T2           ] [ HVV1F3T3
     5'-TTACCAACAATTGAACGACTTGGAGGCTTGTGTTATGCAAGAGGAGAGAGTCGGTGAGACCCC
     3'-TCGAAATGGTTGTTAACTTGCTGAACCTCCGAACACAATACGTTCTCCTCTCTCAGCCACTCTGGGG
         [    HVV1F3B5           ] [     HVV1F3B4             ] [   HV

] [   HVV1F3T4             ] [   HVV1F3T5              ]
     ATTGATGAACGCTGATTCCATCTTGGCTGTCAAGAAGTACTTCAGAAGAATTCAGCTCATTTG-3'
     TAACTACTTGCGACTAAGGTAGAACCGACAGTTCTTCATGAAGTCTTCTTAAGTCGAGTAAACCTAG-5'
     V1F3B3   ] [    HVV1F3B2             ] [     HVV1F3B1 ]
```

Fig. 3

List of oligos synthesized:

| | | |
|---|---|---|
| HVV1F4T1 | PAATTACCTTGTACT | SEQ ID NO:40 |
| HVV1F4T2 | PTGACCGAAAAGAAGTACTCCCCATGTGCC | SEQ ID NO:41 |
| HVV1F4T3 | PTGGGAAGTCGTTAGAGCCGAAATCAT | SEQ ID NO:42 |
| HVV1F4T4 | PGAGATCTTTGTCCTTGTCCACTAACTT | SEQ ID NO:43 |
| HVV1F4T5 | PGCAAGAGAGACTTACCAAGATGGGTGGAG | SEQ ID NO.44 |
| HVV1F4T6 | PACTTGAACTCTCCATAAGCGGCCGCG | SEQ ID NO:45 |
| HVV1F4B1 | PGATCCGCGGCCGCT | SEQ ID NO:46 |
| HVV1F4B2 | PTATGGAGAGTTCAAGTCTCCACCCAT | SEQ ID NO:47 |
| HVV1F4B3 | PCTTGGTAAGTCTCTCTTGCAAGTTAGTGG | SEQ ID NO:48 |
| HVV1F4B4 | PACAAGGACAAAGATCTCATGATTTCGGC | SEQ ID NO:49 |
| HVV1F4B5 | PTCTAACGACTTCCCAGGCACATGGGGAGTA | SEQ ID NO:50 |
| HVV1F4B6 | PCTTCTTTTCGGTCAAGTACAAGGT | SEQ ID NO:51 |

Final ligated product (SEQ ID NO 52)

```
       [  HVV1F4T1  ][    HVV1F4T2        ][      HVV1F4T3
    5'-AATTACCTTGTACTTGACCGAAAAGAAGTACTCCCCATGTGCCTGGGAAGTCGTTAGAGCCGAAATC
    3'-TGGAACATGAACTGGCTTTTCTTCATGAGGGGTACACGGACCCTTCAGCAATCTCGGCTTTAG
           [    HVV1F4B6      ][    HVV1F4B5        ][     HVV1F4

][   HVV1F4T4         ][     HVV1F4T5          ][    HVV1F4T6
    ATGAGATCTTTGTCCTTGTCCACTAACTTGCAAGAGAGACTTACCAAGATGGGTGGAGACTTGAACTCTC
    TACTCTAGAAACAGGAACAGGTGATTGAACGTTCTCTCTGAATGGTTCTACCCACCTCTGAACTTGAGAG
    B4          ][    HVV1F4B3        ][     HVV1F4B2

]
    CATAAGCGGCCGCG-3'
    GTATTCGCCGGCGCCTAG-5'
      ][ HVV1F4B1  ]
```

Fig. 4

SEQ ID NO:

SEQ ID NO:59   CGAAATCATGAGATCTTTGTCCTTGTCCACTAACTTGCAAGAGAGACTTACCAAGATGGGTGGAGACTTGAACTTCCATAAGCGGCCGCCAGCTT   1728
               GCTTTAGTACTCTAGAAACAGGAACAGGTGATTGAACGTTCTCTGAATGGTTCTACCCACCTCTGAACTTGAAGGTATTCGCCGGCGGTCGAA
                          Bgl II                                                              Not I
SEQ ID NO:60    E  I  M  R  S  L  S  L  S  T  N  L  Q  E  R  L  T  K  M  G  G  D  L  N  S  P  A  A  A  S  F
                Xba I                    Mbo II

TCTAGAACAAAAACTCATCTCAGAAGAGGATCTTCCTAGACTTGTAGCCTTGTGACATGACTGTTC   1824
               AGATCTTGTTTTTGAGTAGAGTCTTCTCCTAGAAGGATCTGAACATCGGAATCGTACTGACAAG
                L  E  Q  K  L  I  S  E  E  D  L  N  S  A  V  D  H  H  H  H  H  H  V  C  S  L  R  H  D  C  S
                                            Mbo II

CTCAGTTCAAGTTGGGCACTTACGAGAAGACCGGTCTCTAGATTCTAAGTCAAGAGGATGCAGAATGCCATTTGCCTGAGAGATGCAGGCTTCA   1920
               GAGTCAAGTTCAACCCGTGAATGCTCTTCGGCCAGAACGATCTAAGATTCAGTTCTCCTACAGTCTTACGGTAAACGGACTCTCTACGTCGAAGT
                S  V  Q  V  G  H  L  R  E  D  R  S  C    I  L  I  K  R  M  S  E  C  H  L  P  E  R  C  R  L  H
                                                          Mbo II

TTTTTGATACTTTTTTATTTGTAACCTATATAGTATATAGATTTTTTTTGTCATTTTGTTTCTTCGTACGAGCTTGCTCCTGATCAGCCTATCTC   2016
               AAAAACTATGAAAAATAAACATTGGATATATCATATATCTAAAAAAACAGTAAAACAGAAGAAGCATGCTCGAACGAGGACTAGTCGGATAGAG
                F  Y  F  F  I  C  N  L  Y  S  I  G  F  F  L  S  F  C  F  F  S  Y  E  L  A  P  D  Q  P  I  S
                Tse I                                                                       Mbo II

GCAGCTGATGAATATCTTGTGTGGAGGGTTTGGGAAAATCATTCGAGTTTGATGTTTTCTTTGTATTTCCCACTCCCTCTTCAGAGTACAGAAGAT   2112
               CGTCGACTACTTATAGAACACATGAACACCATCCCCAAACCCTTTTAGTAAGCTCAAACTACAAAGAAACATAAAGGGTGAGGAGAAGTCTCATGTCTCTA
                Q  L  M  N  I  L  W  G  F  G  K  I  I  R  V  C  F  S  W  Y  F  P  L  L  F  R  V  Q  K  I
                             Mbo II     BamH I                                                     Mbo II

TAAGTGAGACCTTCGTTTGTGCGAGGATCCCCCACACACCAAGCACACATAAATTTCCCTCTTCTTCCTCTAGGGTGTCGTAATTACCGTACTAAAGGTTTG   2208
               ATTCACTCTGGAAGCAAACACGCCTAGGGGGTGTGTGGTTCGTGTGTATCGAGATTTAAAGGGAGAAGAAGGAGATCCCACACAGCAATTAATGGGCATGATTTCCAAAC
                K  D  L  R  L  C  G  S  P  T  H  H  S  F  K  M  F  L  L  F  Y  S  S  R  F  S  R  T  P  R
                Mbo II

CATCGCCGTACCACTTCAAAAACACCCAAGCACACAGCATACATAATTTTCCCTCTTTCTTCCTCTAGGGTGTCGTAATTACCGTACTAAAGGTTTG   2304
               GTAGCGGCATGGTGAAGTTTTGTGGGTTCGTGTCGTATGCTATGTATTAAAAGGGAGAAAGAAGGAGATCCCACAGCATTAATGGGCATGATTTCCAAAC
                I  A  V  P  L  Q  N  T  Q  A  Q  H  T  K  F  S  L  F  L  P  L  G  C  R    L  P  V  L  K  V  W
                                                           Mbo I

GAAAAGAAAAAAAGAGACCGCCTCGTTTCTTTTTCGTCGAAAAAGGCAATAAAAATTTTATCACGTTTCTTCTTGAAATTTTTTTTA   2400
               CTTTTCTTTTTTTCTCTGGCGGAGCAAAGAAAAAGCAGCTTTTTCCGTTATTTTAAAATAGTGCAAAGAACTTTAAAAAAAAAT
                K  K  K  R  P  P  R  F  F  F  F  V  E  K  G  N  K  N  F  Y  H  V  S  F  S  N  F  F

```
                   HgaI
                   |
CCTTGCTTGAGAAGGTTTTGGGACGCTCGAAGGCTTTAATTTGCAAGCTGGAGACCAACATGTGAGCAAAAGGCCAGAACCGTA
GGAACGAACTCTTCCAAAACCTGCGAGCTTCCGAAATTAAACGTTCGACCTTCGTTGTACACTCGTTTCGGTCGTTTCCGGTCCTTGGCAT   3360
 L  A   E  G  F  G  T  L  E  G  F  N  L  Q  A  G  D  Q  H  V  S  K  R  P  A  K  G  Q  E  P
                                                                HgaI
                                                                |
AAAAGGCCGCGTTGCTGGCGTTCTTTCCATAGGCTCCGCCCCCCTGACGAGCATCACAAAAATCGACGCTCAAGTCAGAGGTGGGAACGACAG
TTTTCCGGCGCAACGACCGCAAGAAAGTATCCGAGGCGGGGGGACTGCTCGTAGTGTTTTTAGCTGCGAGTTCAGTTCCACCCTTGGCTGTC   3456
 K  G  R  V  A  G  V  F  P   A  P  P  P   R  A  S  Q  K  S  T  L  K  S  E  V  A  K  P  D  R

GACTATAAAGATACCAGGCGTTCCCCCTGGAAGCTCACGCTGTAGTCGGTATCCTAGTTCGGTGTAGGTCGTTCGTTCGTCTTGCGCTTCTCC
CTGATATTTCTATGGTCCGCAAGGGGGACCTTCGAGTGCGACATCAGCCATAGGATCAAGCCACAGCAAGGCCACATCCAGCAAGCGAAGAGG   3552
 T  I  K  I  P  G  V  S  P  W  K  L  P  R  A  L  S  C  S  D  P  A  A  Y  R  I  P  V  R  L  S  P

CTTCGGGAAGCGTGGCGTTTCTCAATGCTCACGCTGTAGTTCGGTGTAGGTATCTCAGTTCGCTCGTTCGTCTCAAGCTGGGCTGTGCACGAACCCG
GAAGCCCTTCGCACCGCGAAAGAGTTACGAGTGCGACATCCATAGAGATCAAGCCACATCCAGCAAGCGAGGTTCGACCCGACACGTGCTTGGGG   3648
 F  G  K  R  G  A  F  S  M  L  T  L  V  S  Q  F  G  V  G  R  S  L  Q  A  G  L  C  A  R  T  P
     TseI                                                              TseI
     |                                                                  |
CCGTTCAGCCCGACCGCTGCGCTTATCCGGTAACTATCGTCTTGAGTCCAACCCGTAAGACACGACTTATCGCCACTGGCAGCAGCCACTGGTA
GGCAAGTCGGGCTGGCGACGCGAATAGGCCATTGATAGCAGAACTCAGTTGGGCATTCTGTGCTGAATAGCGGTGACCGTCGTCGGTGACCAT   3744
 R  S  A  R  P  L  R  L  I  R  L  S  S  V  Q  P  G  K  T  R  L  I  A  T  G  S  S  H  W

ACAGGATTAGCAGAGCGAGGTATGCGAGGCGGTTGAGGCGGTGTACAGAGTTCTTGAAGTGTGGCCTAACTACGGCTACACTAGAAGGACAGTATTGGTATCT
TGTCCTAATCGTCTCGCTCCATACGCTCCGCCAACTCCGCCACATGTCTCAAGAACTTCACCACCGGATTGATGCGATGCTGTCATAAACCATAGA   3840
 Q  D  Q  S  E  V  C  R  R  C  Y  R  V  L  E  V  V  A  L  R  L  H  K  D  S  I  W  Y  L
                                                                       MboII
                                                                       |
GCGCTCTGCTGAAGCCAGTTACCTTCGGAAAAAAGAGTTGTAGCTCTTGATCCGGCAACAAACCACCGCTGGTAGCGGTGGTTTTTTTGTTTGCA
CGCGAGACGACTTCGGTCAATGGAAGCCTTTTTCTCAACATCGAGAACTAGGCCGTTGTTTGGTGGCGACCATCGCCACCATCGCCACCAAAAAAACAAACGT   3936
 R  S  A  E  E  A  S  Y  L  R  K  K  S  W  L  I  R  Q  T  N  H  R  W  R  W  F  F  C  L  Q
     TseI                                                              HgaI
     |                                                                  |
AGCAGCAGATTACGCGCAGAAAAAAGGATCTCAAGAAGATCCTTTGATCTTTTCTACGGGGTCTCAGCCTCACTGGAACGAAAACTCACCTTAAG
TCGTCGTCTAATGCGCGTCTTTTTTCCTAGAGTTCTTCTAGGAAACTAGAAAAGATGCCCCAGAGTCGGAGTGACCTTGCTTTTGAGTGGAATTC   4032
 A  A  D  Y  A  Q  K  K  R  I  S  R  R  S  F  D  L  F  Y  G  V  R  S  V  E  R  K  L  T  L  R

GGATTTTGGTCATGAGATC
CCTAAAACCAGTACTCTAG   4051
 D  F  G  H  E  I
```

Fig. 5C

HVV Amino Acid Sequence

CDLPETHSLDNRRTLMLLAQMSRISPSSCLMDRHDFGFPQEEFDGNQFQKAPAISVLH
ELIQQIFNLFTTKDSSAAWDEDLLDKFCTELYQQLNDLEACVMQEERVGETPLMNAD
SILAVKKYFRRITLYLTEKKYSPCAWEVVRAEIMRSLSLSTNLQERLTKMGGDLNSP (SEQ ID NO:53)

Protein Information

Molecular Weight 19816.67 Daltons
    172 Amino Acids
    18 Strongly Basic(+) Amino Acids (K,R)
    26 Strongly Acidic(-) Amino Acids (D,E)
    56 Hydrophobic Amino Acids (A,I,L,F,W,V)
    50 Polar Amino Acids (N,C,Q,S,T,Y)

4.800 Isolectric Point
    -7.714 Charge at PH 7.0

Total number of bases translated is 519
    % A = 27.36    [142]
    % G = 21.97    [114]
    % T = 28.90    [150]
    % C = 21.77    [113]
    % Ambiguous = 0.00    [0]

% A+T = 56.26    [292]
    % C+G = 43.74    [227]

Davis,Botstein,Roth Melting Temp C. 81.87
    Wallace Temp C    1718.00

Fig. 6A

Codon usage:

| | | | | | | | | | | | | | | |
|---|---|---|---|---|---|---|---|---|---|---|---|---|---|---|
| gca | Ala(A) | 0 | # | cag | Gln(Q) | 0 | # | uug | Leu(L) | 20 | # | uaa | Ter(.) | 1 |
| gcc | Ala(A) | 4 | # | --- | Gln(Q) | 10 | # | --- | Leu(L) | 23 | # | uag | Ter(.) | 0 |
| gcg | Ala(A) | 0 | # | gaa | Glu(E) | 6 | # | aaa | Lys(K) | 0 | # | uga | Ter(.) | 0 |
| gcu | Ala(A) | 6 | # | gag | Glu(E) | 8 | # | aag | Lys(K) | 8 | # | --- | Ter(.) | 1 |
| --- | Ala(A) | 10 | # | --- | Glu(E) | 14 | # | --- | Lys(K) | 8 | # | aca | Thr(T) | 0 |
| aga | Arg(R) | 10 | # | gga | Gly(G) | 1 | # | aug | Met(M) | 7 | # | acc | Thr(T) | 5 |
| agg | Arg(R) | 0 | # | ggc | Gly(G) | 0 | # | --- | Met(M) | 7 | # | acg | Thr(T) | 0 |
| cga | Arg(R) | 0 | # | ggg | Gly(G) | 0 | # | uuc | Phe(F) | 7 | # | acu | Thr(T) | 5 |
| cgc | Arg(R) | 0 | # | ggu | Gly(G) | 4 | # | uuu | Phe(F) | 1 | # | --- | Thr(T) | 10 |
| cgg | Arg(R) | 0 | # | --- | Gly(G) | 5 | # | --- | Phe(F) | 8 | # | ugg | Trp(W) | 2 |
| cgu | Arg(R) | 0 | # | cac | His(H) | 3 | # | cca | Pro(P) | 6 | # | --- | Trp(W) | 2 |
| --- | Arg(R) | 10 | # | cau | His(H) | 0 | # | ccc | Pro(P) | 0 | # | uac | Tyr(Y) | 4 |
| aac | Asn(N) | 7 | # | --- | His(H) | 3 | # | ccg | Pro(P) | 0 | # | uau | Tyr(Y) | 0 |
| aau | Asn(N) | 0 | # | aua | Ile(I) | 0 | # | ccu | Pro(P) | 1 | # | --- | Tyr(Y) | 4 |
| --- | Asn(N) | 7 | # | auc | Ile(I) | 3 | # | --- | Pro(P) | 7 | # | gua | Val(V) | 0 |
| gac | Asp(D) | 8 | # | auu | Ile(I) | 4 | # | agc | Ser(S) | 0 | # | guc | Val(V) | 3 |
| gau | Asp(D) | 4 | # | --- | Ile(I) | 7 | # | agu | Ser(S) | 0 | # | gug | Val(V) | 0 |
| --- | Asp(D) | 12 | # | cua | Leu(L) | 0 | # | uca | Ser(S) | 0 | # | guu | Val(V) | 3 |
| ugc | Cys(C) | 0 | # | cuc | Leu(L) | 0 | # | ucc | Ser(S) | 5 | # | --- | Val(V) | 6 |
| ugu | Cys(C) | 5 | # | cug | Leu(L) | 0 | # | ucg | Ser(S) | 0 | # | nnn | ???(X) | 0 |
| --- | Cys(C) | 5 | # | cuu | Leu(L) | 3 | # | ucu | Ser(S) | 9 | # | TOTAL | | 173 |
| caa | Gln(Q) | 10 | # | uua | Leu(L) | 0 | # | --- | Ser(S) | 14 | # | | | |

Fig. 6B

```
SEQ ID NO:54      C Y L S E T L M L D A R E N L K L L D R M N R L S P H S C L    Majority
                                    10              20              30
SEQ ID NO:55   1  C Y L S E R L M L D A R E N L K L L D R M N R L S P H S C L    IFN-T.OTT.AASEQ.ER
SEQ ID NO:56   1  C Y L S R K L M L D A R E N L K L L D R M N R L S P H S C L    OTP.Y00287.AA
SEQ ID NO:57   1  C D L P E T H S L D N R R T L M L L A Q M S R I S P S S C L    IFNalphaD.AA
SEQ ID NO:1    1  C D L P E T H S L D N R R T L M L L A Q M S R I S P S S C L    HVV.AA
SEQ ID NO:58   1  C Y L S R K L M L D A R E N L K L L D R M N R L S P H S C L    NLV.AA M D R H D F G F P Q E E F D G N Q F Q K A P A I S V L H E L    Majority
                                    40              50              60
              31  Q D R K D F G L P Q E M V E G D Q L Q K D Q A F P V L Y E M    IFN-T.OTT.AASEQ.ER
              31  Q D R K D R G L P Q E M V E G D Q L Q K D Q A F P V L Y E M    OTP.Y00287.AA
              31  M D R H D F G F P Q E E F D G N Q F Q K A P A I S V L H E L    IFNalphaD.AA
              31  M D R H D F G F P Q E E F D G N Q F Q K A P A I S V L H E L    HVV.AA
              31  M D R H D F G F P Q E E F D G N Q F Q K A P A I S V L H E L    NLV.AA I Q Q I F N L F T T K D S S A A W D E D L L D K F C T E L Y    Majority
                                    70              80              90
              61  L Q Q S F N L F Y T E H S S A A W D T T L L E Q L C T G L Q    IFN-T.OTT.AASEQ.ER
              61  L Q Q S F N L F Y T E H S S A A W D T T L L E Q L C T G L Q    OTP.Y00287.AA
              61  I Q Q I F N L F T T K D S S A A W D E D L L D K F C T E L Y    IFNalphaD.AA
              61  I Q Q I F N L F T T K D S S A A W D E D L L D K F C T E L Y    HVV.AA
              61  I Q Q I F N L F T T K D S S A A W D E D L L D K F C T E L Y    NLV.AA Q Q L N D L E A C V M Q E E R V G E T P L M N A D S I L A V    Majority
                                    100             110             120
              91  Q Q L D H L D T C R G Q V M G E E D S E L G N M D P I V T V    IFN-T.OTT.AASEQ.ER
              91  Q Q L D H L D T C R G Q V M G E E D S E L G N M D P I V T V    OTP.Y00287.AA
              91  Q Q L N D L E A C V M Q E E R V G E T P L M N A D S I L A V    IFNalphaD.AA
              91  Q Q L N D L E A C V M Q E E R V G E T P L M N A D S I L A V    HVV.AA
              91  Q Q L N D L E A C V M Q E E R V G E T P L M N A D S I L A V    NLV.AA K K Y F R R I T L Y L T E K K Y S P C A W E V V R A E I M R    Majority
                                    130             140             150
             121  K K Y F Q G I Y D Y L Q E K G Y S D C A W E I V R V E M M R    IFN-T.OTT.AASEQ.ER
             121  K K Y F Q G I Y D Y L Q E K G Y S D C A W E I V R V E E M R    OTP.Y00287.AA
             121  K K Y F R R I T L Y L T E K K Y S P C A W E V V R A E I M R    IFNalphaD.AA
             121  K K Y F R R I T L Y L T E K K Y S P C A W E V V R A E I M R    HVV.AA
             121  K K Y F R R I T L Y L T E K K Y S P C A W E V V R A E I M R    NLV.AA S L S L S T N L Q E R L T K M G G D L N S P                    Majority
                                    160             170
             151  A L T V S T T L Q K R L T K M G G D L N S P                    IFN-T.OTT.AASEQ.ER
             151  A L T V S T T L Q K R L T K M G G D L N S P                    OTP.Y00287.AA
             151  S L S L S T N L Q E R L R R K E                                IFNalphaD.AA
             151  S L S L S T N L Q E R L T K M G G D L N S P                    HVV.AA
             151  S L S L S T N L Q E R L R R K E                                NLV.AA
```

Fig. 10

```
                            SEQUENCE LISTING

<160> NUMBER OF SEQ ID NOS: 2

<210> SEQ ID NO 1
<211> LENGTH: 172
<212> TYPE: PRT
<213> ORGANISM: Artificial Sequence
<220> FEATURE:
<223> OTHER INFORMATION: hybrid interferon

<400> SEQUENCE: 1

Cys Asp Leu Pro Glu Thr His Ser Leu Asp Asn Arg Arg Thr Leu Met
1               5                   10                  15

Leu Leu Ala Gln Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Leu Ser Thr Asn Leu Gln Glu
145                 150                 155                 160

Arg Leu Thr Lys Met Gly Gly Asp Leu Asn Ser Pro
                165                 170

<210> SEQ ID NO 2
<211> LENGTH: 519
<212> TYPE: DNA
<213> ORGANISM: Artificial Sequence
<220> FEATURE:
<223> OTHER INFORMATION: hybrid interferon

<400> SEQUENCE: 2
tgtgatttgc cagagactca ctctttggac aacagaagaa ctttgatgct tttggcccaa     60
atgtctagaa tctctccatc ctcttgtttg atggatagac acgatttcgg tttcccacaa    120
gaagaatttg acggtaacca attccaaaag gctcctgcta tttctgtttt gcacgagttg    180
attcaacaaa ttttcaactt gttcaccact aaggactctt ctgctgcctg ggacgaagac    240
ttgttggaca agttctgtac tgagctttac caacaattga acgacttgga ggcttgtgtt    300
atgcaagagg agagagtcgg tgagacccca ttgatgaacg ctgattccat cttggctgtc    360
aagaagtact tcagaagaat taccttgtac ttgaccgaaa agaagtactc cccatgtgcc    420
tgggaagtcg ttagagccga aatcatgaga tctttgtcct tgtccactaa cttgcaagag    480
agacttacca agatgggtgg agacttgaac tctccataa                           519
```

HYBRID INTERFERON/INTERFERON TAU PROTEINS, COMPOSITIONS AND METHODS OF USE

This application claims priority to U.S. Provisional Application No. 60/311,866, filed Aug. 12, 2001, which is incorporated herein by reference.

FIELD OF THE INVENTION

The present invention relates to hybrid interferon proteins consisting of a C-terminal region derived from interferon-τ and a region derived from another interferon.

REFERENCES

Akiyama, K. et al. (1993) A clinical trial of recombinant bovine interferon alpha 1 for the control of bovine respiratory disease in calves. J. Vet. Med. Sci. 55:3, 449–452.

Ausubel, F. M., et al. (1992) in Current Protocols in Molecular Biology.

Babiuk, L. A. (1987) Use of recombinant bovine alpha interferon in reducing respiratory disease induced by bovine herpes virus type 1. Antimicrob. Agents Chemother. 31:5, 752–757.

Bacila et al. eds. (1978) Biochemistry and Genetics of Yeast.

Balzarini, J, et al., Biochem. Biophys. Res. Commun. 178:563–569 (1991).

Bartol, F. F., et al., Biol. Reprod. 33:745–759 (1985).

Bayne, M. L. et al., Gene 66:235–244 (1988).

Bazer, F. W., and Johnson, H. M., Am. J. Reprod. Immunol. 26:19–22 (1991).

Bazer, F. W., et al., PCT publication WO/94/10313, published May 11, 1994.

Beames, et al., Biotechniques 11:378 (1991).

Benvegnu, L., et al., Cancer 83:901–909 (1998).

Berenguer M., et al., Adv. Gastroenterol. Hepatol. Clin. Nutr. 1:2–21 (1996).

Bitter et al. (1984) Proc. Natl. Acad. Sci. 81:5330–5334.

Brake, A. J., et al. (1984) Alpha-factor-directed synthesis and secretion of mature foreign proteins in Saccharomyces cerevisiae. Proc. Natl. Acad. Sci. USA 81:4642–4646.

Breitling, R. et al. (1989) Secretory expression in Escherichia coli and Bacillus subtilis of human interferon alpha genes directed by staphylokinase signals. Mol. Gen. Genet. 217:2–3, 384–91.

Brierley, R. A. (1998) Secretion of recombinant human insulin-like growth factor 1 (IGF-1). Methods Mol. Biol. 103, 149–177.

Brocca, S., et al. (1998) Design, total synthesis, and functional overexpression of the Candida rugosa lip1 gene coding for a major industrial lipase. Protein Sci. 7, 1415–1422.

Cereghino, J. L. and Cregg, J. M. (2000) Heterologous protein expression in the methylotrophic yeast Pichia pastoris. FEMS Microbiology Reviews 24, 45–66.

Charlier, M., et al., Mol. Cell Endocrinol. 76:161–171 (1991).

Cheng, et al. (1997) The clinical study on treatment of hepatic fibrosis of hepatitis B by IFN-alpha 1 and Chinese medical preparation. Chung Kuo Chung His I Chieh Ho Tsa Chih 17:8, 453–455.

Choo, Q.-L., et al., Science 244, 359–362 (1989).

Choo, Q.-L., et al., Proc. Natl. Acad. Sci. U.S.A. 88, 2451–2455 (1991).

Clarke, B. E., Baillieres Best Pract. Res. Clin. Gastroenterol. 14:293–305 (2000).

Cohen et al. (1980) Proc. Natl. Acad. Sci. USA 77:1078.

Cotler, S. J., et al., J. Viral Hepatitis 7:211–217 (2000).

Crawford-Miksza, L. and David Schnurr, D. (1994) Quantitative Colorimetric Microneutralization Assay for Characterization of Adenoviruses, J. Clinical Microbiology 32(9):2331–2334.

Cregg, J. M. and Madden, K. R. (1989) Use of site-specific recombination to regenerate selectable markers. Mol. Gen. Genet. 219, 320–323.

Cregg, J. M. and Russell, K. A. (1998) Transformations Methods. Mol. Biol. 103, 27–39.

Cregg, J. M., et al. (1985) Pichia pastoris as a host system for transformations. Mol. Cell. Biol. 5, 3376–3385.

Cregg, J. M., et al. (1988) Development of the methylotrophic yeast, Pichia pastoris, as a host system for the production of foreign proteins. Dev. Ind. Microbiol. 23, 33–41.

Cregg, J. M., et al. (1989) Functional characterization of the two alcohol oxidase genes from the yeast Pichia pastoris. Mol. Cell. Biol. 5, 111–1121.

Cregg, J. M., et al. (1993) Recent advances in the expression of foreign genes in Pichia pastoris. Bio/Technology 11:905–910.

Clare, J. J., et al. (1991) Production of mouse epidermal growth factor in yeast: high-level secretion using Pichia pastoris strains containing multiple gene copies. Gene 105, 205–212.

Cross, J. C., and Roberts, R. M., Proc. Natl. Acad. Sci. USA 88:3817–3821 (1991).

Dayhoff et al. (1978) in Atlas of Protein Sequence and Structure (Natl. Biomed. Res. Found., Washington, D.C.).

De Maeyer, E. et al. (1982) Expression of a chemically synthesized human alpha 1 interferon gene. Proc. Natl. Acad. Sci. USA 79:14, 4256–4259.

Deutscher, (1990) Methods in Enz. 182.

Di Bisceglie, A. M., et al., Hepatology 16:649–654 (1992).

Dieperink, E., et al., Am. J. Psychiatry 157:867–876 (2000).

Ecker, D. J., et al., J. Biol. Chem. 264:7715–7719 (1989).

Elliott et al. (1983) Proc. Natl. Acad. Sci. USA 80:7080–7084

Ellis, S. B., et al. (1985) Isolation of alcohol oxidase and two other methanol regulatable genes from the yeast Pichia pastoris. Mol. Cell. Biol. 9, 1316–1323.

Feher, Z., et al., Curr. Genet. 16:461 (1989).

Fernandez H., et al., Eur. J. Epidemiol. 2:1–14 (1986).

Godkin, J. D., et al., J. Reprod. Fertil. 65:141–150 (1982).

Gnatek, G. G., et al, Biol. Reprod. 41:655–664 (1989).

Henikoff et al. (1981) Nature 283:835.

Higgins, D. R., et al. (1998) Small vectors for expression based on dominant drug resistance with direct multicopy selection. Methods Mol. Biol. 103, 41–53.

Hitzeman, R. A., et al., U.S. Pat. No. 4,775,622, issued Oct. 4, 1988.

Helmer, S. D., et al., J. Reprod. Fert. 79:83–91 (1987).

Hollenberg et al. (1981) Curr. Topics Microbiol. Immunol. 96:119.

Horiike N., et al., C. Oncol. Rep. 5:1171–1174 (1998).

Houglum, Clin. Pharm. 2:20–28 (1983).

Imakawa, K., et al., Nature 330:377–379 (1987).

Imakawa, K., et al., Mol. Endocrinol. 3:127 (1989).

Jarpe, M. A., et al., Protein Engineering 7:863–867 (1994).

Jimenez-Saenz, M., et al., *J. Gastroenterology and Hepatology* 15:567–569 (2000).

Jin, X. Y. (1992) A clinical investigation of rHuIFN alpha-1 in the treatment of herpes simplex virus keratitis. Chung Hua Yen Ko Tsa Chih 28:3, 134–137.

Julius et al. (1983) Cell 32:839–852

Klemann, S. W., et al., *Nuc. Acids Res.* 18:6724 (1990).

Koskinas J., et al., *J. Med. Virol.* 45:29–34 (1995).

Kunkel (1985) Proc. Natl. Acad. Sci. USA 82:488–492.

Kunkel et al. (1987) Methods Enzymol. 154:367–382.

Lechner, F., et al., *J. Exp. Med.* 191:1499–1512 (2000).

Liu, H., et al. (1992) An efficient screen for peroxisome-deficient mutants of *Pichia pastoris.* J. Bacteriol. 174, 4943–4951.

Liu, H., et al. (1995) PER3, a gene required for peroxisome biogenesis in *Pichia pastoris,* encodes a peroxisomal membrane protein involved in protein import. *J. Biol. Chem.* 270, 10940–10951.

Ludwig, D. L., et al., *Gene* 132:33 (1993).

Magrin, S., et al., *Hepatology* 19, 273–279 (1994).

Maniatis, T., et al., in *MOLECULAR CLONING: A LABORATORY MANUAL,* Cold Spring Harbor Laboratory, Cold Spring Harbor, N.Y. (1982).

Martal, J., et al., *J. Reprod. Fertil.* 56:63–73 (1979).

Martin, E. W., in *DISPENSING OF MEDICATION: A PRACTICAL MANUAL ON THE FORMULATION AND DISPENSING OF PHARMACEUTICAL PRODUCTS* (Mack Publishing Co., Easton, Pa.), 1976.

Mercereau-Puigalon et al. (1980) Gene 11:163.

Mullis, K. B., U.S. Pat. No. 4,683,202, issued 28, Jul. 1987.

Mullis, K. B., et al., U.S. Pat. No. 4,683,195, issued 28, Jul. 1987.

Noisakran, S. and Carr, D. J. J. (2000) Plasmid DNA encoding IFN-α1 antagonizes herpes simplex virus type 1 ocular infection through $CD4^+$ and $CD8^+$ T Lymphocytes. *Journal of Immunology* 164(12):6435–43.

Noisakran, S., et al. (1999) Ectopic expression of DNA encoding IFN-α1 in the cornea protects mice from herpes simplex virus type 1-induced encephalitis. *J Immunology* 162(7):4184–90.

Oeda, K., et al., U.S. Pat. No. 4,766,068, issued Aug. 23, 1988.

Ott, T. L., et al., *J. IFN Res.* 11:357–364 (1991).

Panthier et al. (1980) Curr. Genet. 2:109.

Pawlotsky, J-M., et al., *J. Interferon and Cytokine Res.* 15:857–862 (1995).

Pearson, W. R. and Lipman, D. J., *PNAS* 85:2444–2448 (1988).

Pearson, W. R., *Methods in Enzymology* 183:63–98 (1990).

Pontzer C. H., et al. (1995) Measurement of interferons. Meth. Neurosci. 24:3–9.

Raemaekers, R. J. M., et al. (1999) Functional phytohaemagglutinin (PHA) and *Galanthus nivalis* agglutinin (GNA) expressed in *Pichia pastoris:* correct N-terminal processing and secretion of heterologous proteins expressed using the PHA-E signal peptide. Eur. J. Biochem. 65, 394–403.

Reilly, P. R., et al., *BACULOVIRUS EXPRESSION VECTORS: A LABORATORY MANUAL,* 1992.

Riesenberg, D. et al. (1990) High cell density fermentation of recombinant *Escherichia coli* expressing human interferon alpha 1. Appl. Microbiol. Biotechnol. 34:1, 77–82.

Roberts, R. M., et al., *Endocrin. Rev.* 13:432–452 (1992).

Rose and Harrison, eds. (1987) *The Yeasts* ($2^{nd}$ ed.).

Rutter, W. J., et al., U.S. Pat. No. 4,769, 238, issued Sep. 6, 1988.

Saito, H., et al., *J. Viral Hepatitis* 7:64–74 (2000).

Sambrook, J., et al. (1989) Molecular Cloning: A Laboratory Manual. Spring Harbor, N.Y.: Cold Spring Harbor Laboratory Press.

Scopes, (1982) Protein purification: principles and practice. Springer-Verlag, New York.

Sears, I. B., et al. (1998) A versatile set of vectors for constitutive and regulated gene expression in *Pichia pastoris.* Yeast 14, 783–790.

Shaw, K. J., et al., *DNA* 7:117 (1988).

Shen, L. P., et al., *Sci. Sin.* 29:856 (1986).

Shen, S., et al. (1998) A strong nitrogen source-regulated promoter for controlled expression of foreign genes in the yeast *Pichia pastoris. Gene* 216, 93–102.

Shepherd, et al. (1998) Prospective randomized trial of two dose levels of interferon alpha with zidovudine for the treatment of Kaposi's sarcoma associated with human immunodeficiency virus infection: a Canadian HIV Clinical Trials Netword Study. J. Clin. Oncol. 16:5, 1736–1742.

Shindo, M., et al., *Hepatology* 9:715–719 (1989)

Singh et al. (1983) Nucleic Acids Res. 11:4049–4063

Singh, A. et al. (1984) Synthesis, secretion and processing of alpha-factor-interferon fusion proteins in yeast. Nucleic Acids Res. 12:23, 8927–8938.

Smith et al. (1985) Science 229:1219–1229.

Skinner et al., eds. (1980) *Biology and Activities of Yeast* (Soc. App. Bacteriol. Symp. Series No. 9).

Stewart, H. J., et al,. *Mol. Endocrinol.* 2:65 (1989).

Strathern et al., eds. (1981) The Molecular Biology of the Yeast Saccharomyces.

Thill, G. P., et al. (1990) Positive and negative effects of multicopy integrated expression vectors on protein expression in *Pichia pastoris.* In: Proceedings of the Sixth International Symposium on the Genetics of Microorganisms (Heslot, H., et al., Eds.), Vol. 2, pp. 477–490. Societe Francaise de Microbiologie, Paris.

Trepo, C., *J. Viral Hepatitis* 7:250–257 (2000).

Tyring, et al., Interferon: Principles and Medical Applications, $1^{st}$ Edition, Section VIII., pgs 399–408, 1992.

Tschopp, J. F., et al. (1987). Expression of the *LacZ* gene from two methanol-regulated promoters in *Pichia pastoris. Nucleic Acids Res.* 15, 3859–3876.

Vallet, J. L., et al., *Biol. Reprod.* 37:1307 (1987).

Van Heeke, G., et al. (1996) High yield expression and secretion of the ovine pregnancy recognition hormone interferon-τ by *Pichia pastoris. J. Interferon and Cytokine Res.* 16:119–126.

Walker and Gaastra, eds. (1983) Techniques in Molecular Biology (MacMillan Publishing Company, New York).

Walter, M. R., et al. (1998) Review of recent developments in the molecular characterization of recombinant alpha Interferons on the 40th anniversary of the discovery of interferon. Cancer Biotherapy and Radiopharmaceuticals 13:3, 143–154.

Waterham, H. R., et al. (1996). The *Pichia pastoris* PER6 gene product is a peroxisomal integral membrane protein essential for peroxisome biogenesis and has sequence similarity to the Zellweger syndrome protein PAF-1. Mol. Cell. Biol. 16, 2527–2536.

Waterham, H. R., et al. (1997) Isolation of the *Pichia pastoris* glyceraldehyde-3-phosphate dehydrogenase gene and regulation and use of its promoter. *Gene* 186, 37–44.

Whaley, A. E., et al., *J. Biol. Chem.* 269:10864–10868 (1994).

White, C. E., et al. (1995) Large-scale expression, purification and characterization of small fragments of thrombomodulin: the roles of the sixth domain and of methionine 388. *Protein Eng.* 8, 1177–1187.

Wu, D. A., et al., *DNA* 10:201 (1991).

Sequence Listing

The present application contains a paper copy of a sequence listing in accordance with 37 C.F.R. §§1.822–1.833, and a copy of the sequence listing in computer readable form in accordance with 37 C.F.R. §1.824, each of which is hereby incorporated herein by reference in its entirety. The information in computer readable form is identical to the paper copy of the sequence listing.

BACKGROUND OF THE INVENTION

Interferons (IFNs) are a family of structurally and functionally related proteins that exhibit pleiotropic effects on the growth and function of a variety of cell types. Since their discovery as antiviral agents in 1957, IFNs have been shown to exhibit various potent immunomodulatory effects, including regulation of natural killer cell activity and modulation of major histocompatibility antigen expression, as well as antiproliferative activity against malignant cells (Walter, et at., 1998).

The major classes of IFN are IFN-α, -β, -τ and -ω, which are also designated type I (acid-stable), and IFN-γ (designated as type II, acid-labile). Table 1, below, summarizes the aspects of the major classes of IFNs.

TABLE 1

Overview of the Interferons

| Aspects | Type I | Type I | Type I | Type II |
|---|---|---|---|---|
| Types | α & ω | β | τ | γ |
| Produced by: | leukocyte | fibroblast | trophoblast | lymphocyte |
| Antiviral | + | + | + | + |
| Antiproliferative | + | + | + | + |
| Pregnancy Signaling | − | − | + | − |

The IFN-α family of proteins is now known to consist of at least 14 genes, including one pseudogene and two genes that encode for the same protein. Thus, there are 12 separate IFN-α proteins produced from the 14 genes. The various IFN-α subtypes share approximately 80% identity at the amino acid sequence level.

Interferon alpha-1 (IFNα1), also known as interferon alpha-D (IFNαD), is a type I interferon of wide research and clinical interest. Recent reports have demonstrated the efficacy of recombinant IFNαD in the treatment of various viral diseases in humans as well as in animals (Noisakran and Carr, 2000; Noisakran, et al., 1999). Due to the clinical and research interest in human IFNαD, different expression systems have been developed and employed.

Expression of recombinant human IFNαD (rHuIFNαD) in 1982 was described for a *Methylophilus methylotrophus* system and an *E. coli* system which both utilized the lac promoter (De Maeyer, 1982). In 1984, Genentech scientists reported a *Saccharomyces cerevisiae* system in which the IFNαD gene fused with the x-factor prepro signal sequence yielded a secreted IFNαD protein that had relatively low biological activity (Singh, 1984). Several years later, in 1989, secretory expression of human interferon genes in *E. coli* and *Bacillus subtilis* (*B. subtilis*), using the staphylokinase heterologous expression-secretion signal, was developed (Breitling, 1989). In these studies, only the *B. subtilis* system, and not the *E. coli* system, was able to secrete rHuIFNαD into the culture medium. A significant improvement on the intracellular expression of rHuIFNαD in *E. coli* was reported in 1990 by the use of a defined medium in a fed batch mode during fermentation that allowed for a more efficient expression of the protein at reduced specific growth rates in *E. coli* However, for over eleven years there has been no additional significant improvements in the production of human IFNαD.

The first IFN-τ to be identified was ovine IFN-τ (OvIFN-τ), as a 18–19 kDa protein. Several isoforms were identified in conceptus (the embryo and surrounding membranes) homogenates (Martal, et al., 1979). Subsequently, a low molecular weight protein released into conceptus culture medium was purified and shown to be both heat labile and susceptible to proteases (Godkin, et al., 1982). OvIFN-τ was originally called ovine trophoblast protein-one (oTP-1) because it was the primary secretory protein initially produced by trophectoderm of the sheep conceptus during the critical period of maternal recognition in sheep. Subsequent experiments have determined that OvIFN-τ is a pregnancy recognition hormone essential for establishment of the physiological response to pregnancy in ruminants, such as sheep and cows (Bazer and Johnson, 1991).

An IFN-τ cDNA obtained by probing a sheep blastocyst library with a synthetic oligonucleotide representing the N-terminal amino acid sequence (Imakawa, et al., 1987) has a predicted amino acid sequence that is 45–55% homologous with IFN-αs from human, mouse, rat and pig and 70% homologous with bovine IFN-αII, now referred to as IFN-Ω. Several cDNA sequences have been reported which may represent different isoforms (Stewart, et al., 1989; Klemann, et al., 1990; and Charlier, M., et al., 1991). All are approximately 1 kb with a 585 base open reading frame that codes for a 23 amino acid leader sequence and a 172 amino acid mature protein. The predicted structure of IFN-τ as a four helical bundle with the amino and carboxyl-termini in apposition further supports its classification as a type I IFN (Jarpe, et al., 1994).

While IFN-τ displays many of the activities classically associated with type I IFNs (see Table 1, above), considerable differences exist between it and the other type I IFNs. The most prominent difference is its role in pregnancy, detailed above. Also different is viral induction. All type I IFNs, except IFN-τ, are induced readily by virus and dsRNA (Roberts, et al., 1992). Induced IFN-α and IFN-β expression is transient, lasting approximately a few hours. In contrast, IFN-τ synthesis, once induced, is maintained over a period of days (Godkin, et al., 1982). On a per-cell basis, 300-fold more IFN-τ is produced than other type I IFNs (Cross and Roberts, 1991).

Other differences may exist in the regulatory regions of the IFN-τ gene. For example, transfection of the human trophoblast cell line JAR with the gene for bovine IFN-τ resulted in antiviral activity while transfection with the bovine IFN-Ω gene did not. This implies unique transacting factors involved in IFN-τ gene expression. Consistent with this is the observation that while the proximal promoter region (from 126 to the transcriptional start site) of IFN-τ is highly homologous to that of IFN-α and IFN-β; the region from −126 to −450 is not homologous and enhances only IFN-τ expression (Cross and Roberts, 1991). Thus, different regulatory factors appear to be involved in IFN-τ expression as compared with the other type I IFNs.

IFN-τ expression may also differ between species. For example, although IFN-τ expression is restricted to a particular stage (primarily days 13–21) of conceptus development in ruminants (Godkin, et al., 1982), preliminary studies suggest that the human form of IFN-τ is constitutively expressed throughout pregnancy (Whaley, et al., 1994).

Significantly, the usefulness of interferons has been limited by the toxicity. Use of interferons in the treatment of cancer and viral disease has resulted in serious side effects. IFN-α was introduced as therapy for chronic hepatitis C in the United States in 1991 and in Japan in 1992 (Saito, et al., 2000). However, use of IFN-α in sufficient dosage to yield clinical efficacy (i.e., at amounts of about 1×10⁶ units/treatment and above) is usually associated with a "flu-like" syndrome characterized by fever, headache, lethargy, arthalgias and myalgias (Tyring, et al., 1992). At doses of 5–10× $10^6$ units/treatment and above, other toxicities, such as nausea, vomiting, diarrhea and anorexia, become more frequent. Neuropsychiatric symptoms have also been reported in association with IFN-α treatment (Dieperink, et al., 2000). In addition, some studies suggest that the efficacy of IFN-α treatment is not dose dependent (Saito, et al., 2000), and that treatment with IFN-α is associated with the development or exacerbation of autoimmune disorders in patients with neoplasms or viral hepatitis (Jimenez-Saenz, et al., 2000).

Thus, there exists a need for an interferon protein with high antiviral activity and low cytotoxicity. The present invention is designed to meet these needs.

SUMMARY OF THE INVENTION

Accordingly, it is an object of the invention to provide, in one aspect, an interferon/interferon-τ hybrid protein including an interferon protein wherein the C-terminal region of said interferon protein is replaced by a C-terminal region of interferon-τ. In one embodiment, the invention provides a non-τ interferon/interferon-τ hybrid protein that includes a non-τ interferon protein wherein the C-terminal region of said non-τ interferon protein is replaced by a C-terminal region of interferon-τ. In another embodiment, the interferon protein is a type I interferon protein. The type I interferon protein may be interferon-α. Preferably, the interferon-α is human interferon-α. In one embodiment, the human interferon-α is human interferon-αD. In yet another embodiment, the interferon protein is interferon-β.

In one embodiment, the hybrid protein is capable of exhibiting lower toxicity relative to the native interferon, e.g. interferon-α in an assay that includes incubating a first sample of PBMCs for seven days in a culture medium comprising at least 2000 antiviral units/ml of the hybrid; incubating a second sample of PBMCs for seven days in a culture medium having an equal concentration, as antiviral units/ml of the native IFN-α; and comparing the percentage of viable cells remaining in the first sample with that in the second sample, whereby a higher percentage of viable cells indicates the relatively lower toxicity of the IFN species in the culture medium.

In one embodiment of the invention, the interferon protein does not have any of the C-terminal region replaced, but instead has a C-terminal region of interferon-τ added onto the full length interferon protein. Thus, the interferon protein would have 0 amino acids of the C-terminus replaced. In another embodiment, the interferon protein has between about 1–30 amino acids of the C-terminus replaced. In yet another embodiment, the interferon protein has between about 1–10 amino acids on the C-terminus replaced. Preferably, the interferon protein has the final four amino acids of the C-terminus replaced. In a related embodiment, the C-terminal region of the human interferon-αD corresponds to a sequence spanning residues 163–166 of SEQ ID NO:57.

In one embodiment, the hybrid protein includes the C-terminal region of interferon-τ and corresponds to a sequence spanning residues 163–172 of interferon-τ (SEQ ID NO:55). Preferably, the interferon protein is human interferon-αD, and the C-terminal region of the human interferon-αD spans residues 163–166 of SEQ ID NO:57, and the C-terminal region of interferon-τ corresponds to a sequence spanning residues 163–172 of interferon-τ (SEQ ID NO:55).

In one embodiment, the hybrid protein has reduced cytotoxicity relative to the cytotoxicity of the interferon or non-τ interferon protein. In another embodiment, the hybrid protein has increased antiviral activity relative to the antiviral activity of the interferon or non-τ interferon protein. In a related embodiment, the hybrid protein has an antiviral activity of at least about 1×10⁸ antiviral units/mg in MDBK/VSV antiviral system. In another related embodiment, the hybrid protein has an antiviral activity of at least about 2×10⁸ antiviral units/mg in MDBK/VSV antiviral system.

The invention contemplates that the interferon-τ protein is a ruminant interferon-τ. In one embodiment, the interferon-τ is ovine or bovine interferon-τ. The invention also contemplates that any of the hybrid proteins described above may be pegylated.

In another aspect, the invention includes a nucleic acid molecule encoding any of the hybrid proteins described above. In yet another aspect, the invention includes a method for making an interferon hybrid protein. The steps involved in practicing the method include placing any of the nucleic acid molecules described above in a recombinant expression system; affecting expression of the nucleic acid molecule so as to produce the hybrid protein; and recovering the hybrid protein. In one embodiment, the recombinant expression system includes *P. pastoris*.

In yet another aspect, the invention includes a pharmaceutical composition that includes a hybrid protein prepared as described above, and a pharmaceutically-acceptable carrier. The composition may also include ribavirin.

The invention also includes, in one aspect, a method of inhibiting viral replication in cells infected with a virus. The method includes contacting the cells with a hybrid protein in an amount effective to inhibit replication of the virus in the cells.

A method of inhibiting the growth of tumor cells is also contemplated. The method includes contacting the tumor cells with a hybrid protein in an amount effective to inhibit their growth.

Another aspect of the invention includes a method of treating an autoimmune disease in a subject. The method includes administering to the subject any of the hybrid proteins prepared as described above in an amount effective to treat the disease.

Yet another aspect of the invention includes a method of treating chronic inflammation in a subject. The method includes administering to the subject any of the hybrid proteins prepared as described above in an amount effective to treat the inflammation.

Still another aspect of the invention includes a method of treating a disease condition responsive to interferon. The method includes administering to a subject having the disease condition any of the hybrid proteins prepared as described above in an amount effective to treat the disease condition.

In any of the methods described above the administering may be performed by an administration method selected from the group consisting of oral, topical, inhalation, nasal and injection.

These and other objects and features of the invention will be more fully appreciated when the following detailed description of the invention is read in conjunction with the accompanying drawings.

BRIEF DESCRIPTION OF THE DRAWINGS

FIG. 1 shows the sequence of the oligonucleotides used to produce HVV Fragment 1, and the final ligated product;

FIG. 2 shows the sequence of the oligonucleotides used to produce HVV Fragment 2, and the final ligated product;

FIG. 3 shows the sequence of the oligonucleotides used to produce HVV Fragment 3, and the final ligated product;

FIG. 4 shows the sequence of the oligonucleotides used to produce HVV Fragment 4, and the final ligated product;

Figure 5B:
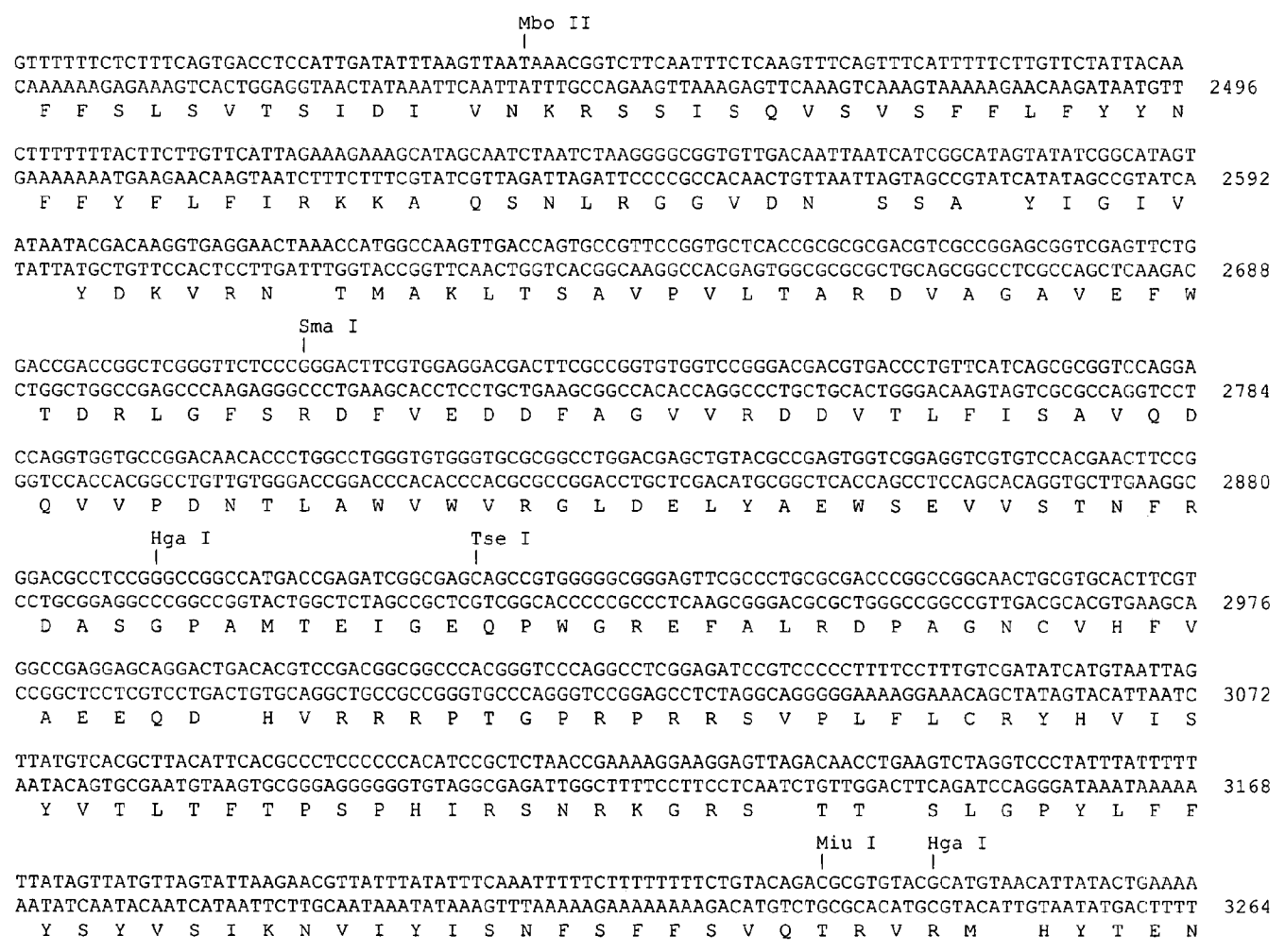

FIGS. 5A–5C show the sequence and selected restriction sites of the HVV-pPICZ-α construct;

FIGS. 6A–6B show selected HVV protein information;

Figure 7:
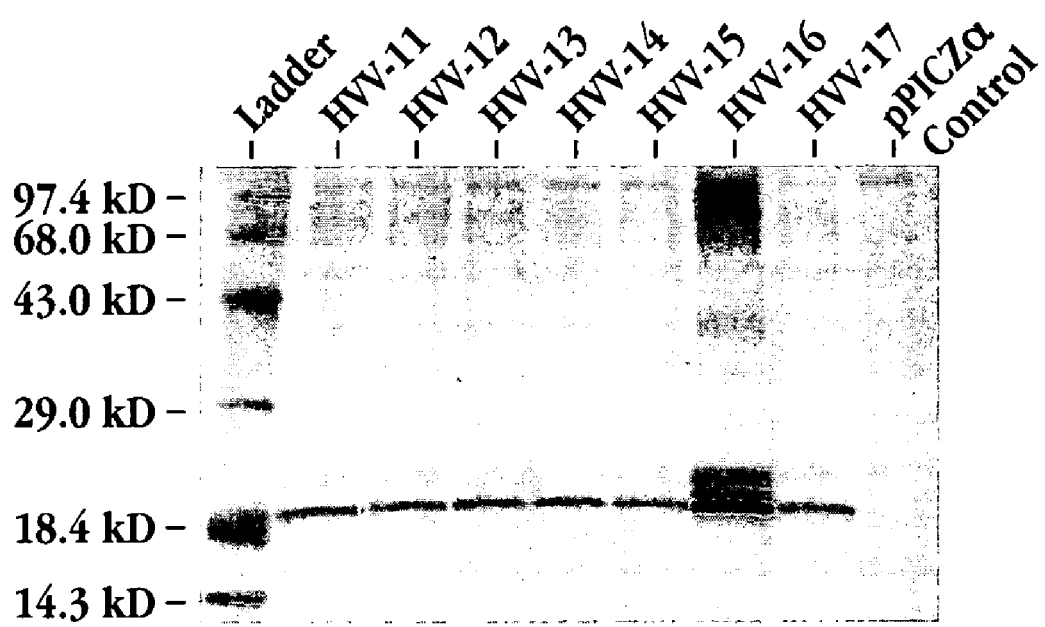
FIG. 7 is a SDS-PAGE gel of *P. pastoris* HVV recombinant culture supernatants after 72 hours of induction with 1% methanol;

FIG. 8 is a SDS-PAGE gel showing the partial purification of HVV protein from *P. pastoris* supernatants.

FIG. 9 illustrates the percent specific cell death of PBMC cells as analyzed by flow cytometry.

FIG. 10 shows the amino acid sequence alignment of selected interferon proteins.

DETAILED DESCRIPTION OF THE INVENTION

I. Definitions

Unless otherwise indicated, all technical and scientific terms used herein have the same meaning as they would to one skilled in the art of the present invention. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

All publications and patents cited herein are expressly incorporated herein by reference for the purpose of describing and disclosing compositions and methodologies which might be used in connection with the invention.

A "heterologous" nucleic acid construct or sequence has a portion of the sequence which is not native to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native cell.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

As used herein, an "expression cassette" or "expression vector" is a nucleic acid construct generated recombinantly or synthetically, with a series of specified nucleic acid elements that permit transcription of a particular nucleic acid in a target cell or in vitro. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded (ds) DNA construct used as a cloning vector, and which forms an extrachromosomal self-replicating genetic element in many bacteria and some eukaryotes.

As used herein, the term "selectable marker-encoding nucleotide sequence" refers to a nucleotide sequence which is capable of expression in host cells and where expression of the selectable marker confers to cells containing the expressed gene the ability to grow in the presence of a corresponding selective agent.

As used herein, the terms "promoter" and "transcription initiator" refer to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

"Chimeric gene" or "heterologous nucleic acid construct", as defined herein refers to a non-native gene (i.e., one that has been introduced into a host) that may be composed of parts of different genes, including regulatory elements. A chimeric gene construct for transformation of a host cell is typically composed of a transcriptional regulatory region (promoter) operably linked to a heterologous protein coding sequence, or, in a selectable marker chimeric gene, to a selectable marker gene encoding a protein conferring antibiotic resistance to transformed host cells. A typical chimeric gene of the present invention, for transformation into a host cell, includes a transcriptional regulatory region that is constitutive or inducible, a protein coding sequence, and a terminator sequence. A chimeric gene construct may also include a second DNA sequence encoding a signal peptide if secretion of the target protein is desired.

A nucleic acid is "operably linked" when it is placed into a functional relationship with another nucleic acid sequence. For example, DNA encoding a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, the term "expression" refers to the process by which a polypeptide is produced based on the nucleic acid sequence of a gene. The process includes both transcription and translation.

The term "signal sequence" refers to a sequence of amino acids at the N-terminal portion of a protein which facilitates the secretion of the mature form of the protein outside the cell. The mature form of the extracellular protein lacks the signal sequence which is cleaved off during the secretion process.

By the term "host cell" is meant a cell that contains a vector and supports the replication, and/or transcription or transcription and translation (expression) of the expression construct. Host cells for use in the present invention can be prokaryotic cells, such as $E.$ $coli$ or eukaryotic cells such as yeast, plant, insect, amphibian, or mammalian cells.

As used herein, the terms "active" and "biologically active" refer to a biological activity associated with a particular target protein, such as the enzymatic activity. It follows that the biological activity of a given protein refers to any biological activity typically attributed to that protein by those of skill in the art.

"Hepatitis C virus or HCV" refers to the viral species of which pathogenic types cause Non-A Non-B Hepatitis (NANBH), and attenuated types or defective interfering particles derived therefrom. The HCV genome is comprised of RNA. RNA containing viruses have relatively high rates of spontaneous mutation reportedly on the order of $10^{-3}$ to $10^{-4}$ per incorporated nucleotide. Since heterogeneity and fluidity of genotype are inherent in RNA viruses, there are multiple types/subtypes, within the HCV species which may be virulent or avirulent. The propagation, identification, detection, and isolation of various HCV types or isolates is documented in the literature.

"Treating" a condition refers to administering a therapeutic substance effective to reduce the symptoms of the condition and/or lessen the severity of the condition.

"Oral" refers to any route that involves administration by the mouth or direct administration into the stomach or intestines, including gastric administration.

"OAS level" refers to the concentration or activity of blood 2',5'-oligoadenylate synthetase (OAS) protein.

By "yeast" is intended ascosporogenous yeasts (Endomycetales), basidiosporogenous yeasts, and yeast belonging to the Fungi imperfecti (Blastomycetes). The ascosporogenous yeasts are divided into two families, Spermophthoraceae and Saccharomycetaceae. The later is comprised of four subfamilies, Schizosaccharomycoideae (e.g., genus Schizosaccharomyces), Nadsonioideae, Lipomycoideae, and Saccharomycoideac (e.g., genera Pichia, Kllyveromyces, and Saccharomyces). The basidiosporogenous yeasts include the genera Leucosporidium, Rhodosporidium, Sporidiobolus, Filobasidium, and Filobasidiella. Yeast belonging to the Fungi Imperfecti are divided into two families, Sporobolomycetacea (e.g., genera Sporoholomyces, Bullera) and Cryptococcaceae (e.g., genus Candida). Of particular interest to the present invention are species within the genera Pichia, Kluyveromyces, Saccharomyces, Schizosaccharomyces, and Candida. Of particular interest is the Pichia species P. pastoris. Since the classification of yeast may change in the future, for the purposes of this invention, yeast shall be defined as described in Skinner et al. In addition to the foregoing, those of ordinary skill in the art are presumably familiar with the biology of yeast and the manipulation of yeast genetics. See, for example, Bacila et al.; Rose and Harrison; Strathern et al; herein incorporated by reference.

The nucleotide sequences of the present invention are useful for producing biologically active mature heterologous proteins of interest in a yeast host cell when operably linked to a yeast promoter. In this manner, the nucleotide sequences encoding the hybrid precursor polypeptides of the invention are provided in expression cassettes for introduction into a yeast host cell. These expression cassettes will comprise a transcriptional initiation region linked to the nucleotide sequence encoding the hybrid precursor polypeptide. Such an expression cassette is provided with a plurality of restriction sites for insertion of the nucleotide sequence to be under the transcriptional regulation of the regulatory regions. The expression cassette may additionally contain selectable marker genes.

A cloning or expression vector may comprise additional elements, for example, the expression vector may have two replication systems, thus allowing it to be maintained in two organisms, for example in human or insect cells for expression and in a prokaryotic host for cloning and amplification.

Both cloning and expression vectors contain a nucleic acid sequence that enables the vector to replicate in one or more selected host cells. Further, for integrating expression vectors, the expression vector contains at least one sequence homologous to the host cell genome, and preferably two homologous sequences that flank the expression construct. The integrating vector may be directed to a specific locus in the host cell by selecting the appropriate homologous sequence for inclusion in the vector. Constructs for integrating vectors are well known in the art.

Cloning and expression vectors will typically contain a selectable marker. Typical selectable marker genes encode proteins that (a) confer resistance to antibiotics or other toxins, for example, ampicillin, neomycin, methotrexate, zeocin or tetracycline, (b) complement auxotrophic deficiencies, or (c) supply critical nutrients not available from complex media, for example, the gene encoding D-alanine racemase for Bacilli.

"IFN-τ" refers to any one of a family of interferon proteins having greater than 70%, or preferably greater than about 80%, or more preferably greater than about 90%, and even more preferably greater than about 95% amino acid homology to the IFN-τ sequences indicated as such in U.S. Pat. No. 5,939,286, which is expressly incorporated by reference herein in its entirety, or to the IFN-τ and ovine IFN-τ sequences presented in FIG. 10. Amino acid homology can be determined using, for example, the ALIGN program with default parameters. This program is found in the FASTA version 1.7 suite of sequence comparison programs (Pearson and Lipman, 1988; Pearson, 1990; program available from William R. Pearson, Department of Biological Chemistry, Box 440, Jordan Hall, Charlottesville, Va.).

"IFN-α" refers to any one of a family of interferon proteins including the IFN-αD amino acid sequence as shown in FIG. 10, and to proteins having amino acid substitutions and alterations such as neutral amino acid substitutions that do not significantly affect the activity of the protein. Preferably the sequence includes the IFN-αD sequence of FIG. 10 and the proteins with greater than about 70%, or preferably greater than about 80%, or more preferably greater than about 90%, and even more preferably greater than about 95% amino acid sequence homology to the sequence shown in FIG. 10. Amino acid homology can be determined using, for example, the ALIGN program with default parameters as described above.

As used herein, the term "IFN expression" refers to transcription and translation of the above-described IFN genes, the products of which include precursor RNA, mRNA, polypeptide, post-translation processed polypeptide, and derivatives thereof. By way of example, assays for IFN expression include standard cytopathic protection assays, Western and Northern blot analysis and reverse transcriptase polymerase chain reaction (RT-PCR) for IFN mRNA.

As used herein, the terms "biological activity of IFN" and "biologically active IFN" refer to any biological activity associated with IFN, or any fragment, derivative, or analog of IFN, such as enzymatic activity, and specifically including antiviral activity which can be measured using standard cytopathic protection assays.

As used herein, the term "modified form of", relative to proteins associated with IFN, means a derivative or variant form of the native protein. That is, a "modified form of" a protein has a derivative polypeptide sequence containing at least one amino acid substitution, deletion or insertion, with amino acid substitutions being particularly preferred. The amino acid substitution, insertion or deletion may occur at any residue within the polypeptide sequence, which interferes with the biological activity of the protein. The corresponding nucleic acid sequence which encodes the variant or derivative protein is considered to be a "mutated" or "modified" form of the gene or coding sequence therefor, and is included within the scope of the invention.

By "variant" is intended a polypeptide derived from the native polypeptide by deletion (so-called truncation) or addition of one or more amino acids to the N-terminal and/or C-terminal end of the native protein; deletion or addition of one or more amino acids at one or more sites in the native polypeptide; or substitution of one or more amino acids at one or more sites in the native polypeptide. Such variants may result from, for example, genetic polymorphism or from human manipulation. Methods for such manipulations are generally known in the art.

For example, amino acid sequence variants of the polypeptide can be prepared by mutations in the cloned DNA sequence encoding any of the hybrid IFNs. Methods for mutagenesis and nucleotide sequence alterations are well known in the art. See, for example, Walker and Gaastra, eds. (1983); Kunkel (1985); Kunkel et al. (1987); and Sambrook et al. (1989). Guidance as to appropriate amino acid substitutions that do not affect biological activity of the protein of interest may be found in the model of Dayhoff et al. (1978), herein incorporated by reference. Conservative substitutions, such as exchanging one amino acid with another having similar properties, may be preferred. Examples of conservative substitutions include, but are not limited to, Gly⇌Ala, Val⇌Ile⇌Leu, Asp⇌Glu, Lys⇌Arg, Asn⇌Gln, and Phe⇌Trp⇌Tyr.

In constructing variants of hybrid IFN, modifications will be made such that variants continue to possess the desired activity. Obviously, any mutations made in the DNA encoding the variant protein must not place the sequence out of reading frame and preferably will not create complementary regions that could produce secondary mRNA structure.

Thus, proteins of the invention include the hybrid IFN/IFN-τ proteins as well as variants thereof. These variants will be substantially homologous and functionally equivalent to the native protein. A variant of a native protein is "substantially homologous" to the native protein when at least about 80%, more preferably at least about 90%, and most preferably at least about 95% of its amino acid sequence is identical to the amino acid sequence of the native protein. A variant may differ by as few as 1, 2, 3, or 4 amino acids. By "functionally equivalent" is intended that the sequence of the variant defines a chain that produces a protein having substantially the same biological activity as the native IFN. Such functionally equivalent variants that comprise substantial sequence variations are also encompassed by the invention. Thus, a functionally equivalent variant of the hybrid IFN protein will have a sufficient biological activity to be therapeutically useful. By "therapeutically useful" is intended effective in achieving a therapeutic goal, as, for example, protection against herpes simplex virus type 1-induced encephalitis.

Methods are available in the art for determining functional equivalence. Biological activity can be measured using assays specifically designed for measuring activity of IFN proteins, including assays described in the present invention and in U.S. Pat. No. 6,204,022, which is expressly incorporated by reference in its entirety herein. Additionally, antibodies raised against the biologically active native protein can be tested for their ability to bind to the functionally equivalent variant, where effective binding is indicative of a protein having a conformation similar to that of the native protein.

II. Hybrid Interferon Fusion Proteins

The present invention employs observations regarding decreased toxicity conferred by the C-terminal region of IFN-τ in support of chimeric DNA constructs used to produce hybrid interferon fusion proteins having a C-terminal portion derived from IFN-τ and a N-terminal portion derived from a non-tau interferon type I polypeptide. Examples of such non-tau interferon type I polypeptides include IFN-β and the various isoforms of IFN-α.

With reference to FIG. 10, such a hybrid interferon fusion protein or polypeptide HVV, which may be encoded by a chimeric nucleic acid molecule or produced via native chemical ligation, has an N-terminus comprising from amino acid position 1 to amino acid position 162 of IFN-αD (SEQ ID NO:57), and a C-terminus comprising from amino acid position 163 to amino acid position 172 of IFN-τ (SEQ ID NO:55). The N-terminal segment contains the N-terminal amino acid sequence of a non-τ interferon polypeptide which may be encoded by a 5' end segment of the chimeric nucleic acid molecule. The C-terminal segment contains the C-terminal amino acid sequence of an IFN-τ polypeptide which may be encoded by a 3' end segment of the chimeric nucleic acid molecule.

The optimal junction or amino acid residue position upstream of which the sequence corresponds to non-τ interferon, and downstream of which corresponds to IFN-τ can be identified by the methods described herein, using peptides or DNA sequences encoding peptides corresponding to longer and shorter regions within or extending beyond, for example, the IFN-τ residues 163–172 of SEQ ID NO:55, in combination with the functional assays described herein, such as the antiviral assay described in Example 5 and the toxicity assay described in Example 6. It is contemplated that, for example, a hybrid or chimeric interferon of the present invention containing amino acids 1–162 of human IFN-αD and the 10 final C-terminal amino acids of IFN-τ possesses the low toxicity associated with interferon tau along with the biological activity associated or normally ascribed to IFN-α. For example, an IFN-α/IFN-τ hybrid may, for example, reduce the toxicity of IFN-α but not interfere with, or even increase, IFN-α antiviral properties.

Preferred embodiments of the present invention are fusion proteins where the sequence of the N-terminal segment is derived from human IFN-αD, and the C-terminal segment is derived from ovine IFN-τ. Other suitable IFN sequences may be obtained from GenBank or other public sequence depository.

As pointed out above, a considerable advantage contemplated for hybrid interferon fusion protein compositions of the present invention is reduced toxicity of the compositions relative to native non-tau type I interferons that have, for example, been approved as therapeutics. The hybrid compositions may have the same biological activity as the approved non-tau type I IFNs with the decreased cytotoxicity of IFN-τ.

III. Production of Hybrid Interferon Proteins

The invention includes, in one aspect, a method of producing non-τ interferon/interferon-τ hybrid proteins. It has been discovered that when a *P. pastoris* expression host is transformed with a vector containing the proper nucleic acid sequences, production of large amounts of relatively pure and functionally active non-τ interferon/interferon-τ hybrid proteins is possible. Considered below are the steps in practicing the invention.

Sequences, methods and compositions useful in the present invention may be found in U.S. Pat. No. 5,958,402, issued Sep. 28, 1999; U.S. Pat. No. 5,942,223, issued Aug. 24, 1999; Aug. 24, 1999; U.S. Pat. No. 5,738,845, issued Apr. 14, 1998; U.S. Pat. No. 5,939,286, issued Aug. 17, 1999; 6,204,022, issued Mar. 20, 2001; U.S. Pat. No. 5,906,816, issued May 25, 1999; 6,060,450, issued May 9, 2000; and U.S. Pat. No. 6,372,206, issued Apr. 16, 2002; each of which is incorporated by reference in its entirety herein. Additional sequences, methods and compositions useful in the present invention may be found in co-pending U.S. patent application Ser. Nos. 09/910,406, filed Jul. 19, 2001; and 10/137,127, filed May 2, 2002, each of which is incorporated by reference in its entirety herein.

A. *P. pastoris* Host Cells

The host chosen for expression of non-τ interferon/interferon-τ hybrid proteins will preferably be a yeast. The yeast used in the method of the present invention are species within the genera *Pichia*. Of particular interest is the *Pichia* species *P. pastoris*. One exemplary *P. pastoris* strain is X-33.

*P. pastoris* is capable of metabolizing methanol as its sole carbon source by inducing the production of alcohol oxidase (Cregg, 1993). Most *P. pastoris* expression strains have one or more auxotrophic mutations which allow for selection of expression vectors containing the appropriate selectable marker gene upon transformation. Prior to transformation, these strains grow on complex media but require supplementation with the appropriate nutrient(s) for growth on minimal media. *P. pastoris* strains of the present invention include those strains that grow on methanol at the wild-type rate ($Mut^+$), and also those which vary with regard to their ability to utilize methanol because of deletions in one or both AOX genes. Also contemplated are protease-deficient strains that can be effective in reducing degradation of foreign proteins (Brierley, 1998; and White et al., 1995).

The selection of suitable yeast and other microorganism hosts for the practice of the present invention is within the skill of the art. When selecting yeast hosts for expression, suitable hosts may include those shown to have, inter alia, good secretion capacity, low proteolytic activity, and overall vigor. Yeast and other microorganisms are generally available from a variety of sources, including the Yeast Genetic Stock Center, Department of Biophysics and Medical Physics, University of California (Berkeley, Calif.); the American Type Culture Collection (Manassas, Va.); Northern Regional Research Laboratories (Peoria, Ill.); and vendors such as Invitrogen (San Diego, Calif.).

B. Yeast Expression Vector

Expression vectors for use in the present invention comprise a chimeric gene (or expression cassette), designed for operation in yeast, with companion sequences upstream and downstream from the expression cassette. The companion sequences will be of plasmid or viral origin and provide necessary characteristics to the vector to permit the vectors to move DNA from bacteria to the desired yeast host. Suitable transformation vectors are described below. Suitable components of the expression plasmid, including a trancription and translation initiator, a signal sequence, a coding sequence for the hybrid IFN, and suitable transcription and translation terminators are also discussed below. One exemplary construct is the pPICZα-HVV plasmid sequence shown in FIGS. 5A–5C.

i. Transcription & translation initiators

The nucleotide sequences of the present invention are useful for producing biologically active mature heterologous proteins of interest in a yeast host cell when operably linked to a yeast promoter. In this manner, the nucleotide sequences encoding the hybrid precursor polypeptides of the invention are provided in expression cassettes for introduction into a yeast host cell. These expression cassettes will comprise a transcriptional initiation region linked to the nucleotide sequence encoding the hybrid precursor polypeptide. Such an expression cassette is provided with a plurality of restriction sites for insertion of the nucleotide sequence to be under the transcriptional regulation of the regulatory regions.

The transcription initiation region, the yeast promoter, provides a binding site for RNA polymerase to initiate downstream (3') translation of the coding sequence. The promoter may be a constitutive or inducible promoter, and may be native or analogous or foreign or heterologous to the specific yeast host. Additionally, the promoter may be the natural sequence or alternatively a synthetic sequence. By foreign is intended that the transcription initiation region is not found in the native yeast of interest into which the transcription initiation region is introduced.

Suitable native yeast promoters include, but are not limited to the wild-type alpha-factor promoter, which is described in detail below, as well as other yeast promoters. Preferably the promoter is selected from the list including the *P. pastoris* glyceraldehyde 3-phosphate dehydrogenase (GAP), formaldehyde dehydrogenase (FLD1), peroxisomal matrix protein (PEX8), and the GTPase encoding YPT1 promoter. More preferably the promoter is the alcohol oxidase AOX1 promoter.

a. The AOX1 promoter

Although *Pichia* codes for two alcohol oxidase genes, AOX1 and AOX2, the AOX1 gene is responsible for the vast majority of alcohol oxidase activity in the yeast cell (Tschopp, et al., 1987; Ellis, et al., 1985; and Cregg, et al., 1989). Expression of the AOX1 gene is tightly controlled at the level of transcription by the AOX1 promoter. In methanol-grown cells, ~5% of poly(A)$^+$ RNA is from AOX1; however, in cells grown on most other carbon sources, AOX1 message is undetectable (Cregg, et al., 1988).

The regulation of the AOX1 gene appears to involve two mechanisms: a repression/derepression mechanism plus an induction mechanism, similar to the regulation of the *S. cerevisiae* GAL1 gene. Unlike GAL1 regulation, the absence of a repressing carbon source, such as glucose in the medium, does not result in substantial transcription of AOX1. The presence of methanol is essential to induce high levels of transcription (Tschopp, et al., 1987).

b. The GAP Promoter

Both northern and reporter activation results indicate that the *P. pastoris* GAP gene promoter provides strong constitutive expression on glucose at a level comparable to that seen with the AOX1 promoter (Waterham, et al., 1997). GAP promoter activity levels in glycerol- and methanol-grown cells are approximately two-thirds and one-third of the level observed for glucose, respectively. The advantage of using the GAP promoter is that methanol is not required for induction, nor is it necessary to shift cultures from one carbon source to another, making strain growth more straightforward. However, since the GAP promoter is constitutively expressed, it may not be a good choice for the production of proteins that are toxic to yeast.

c. The FLD1 Promoter

The FLD1 gene encodes a glutathione-dependent formaldehyde dehydrogenase, a key enzyme required for the metabolism of certain methylated amines as nitrogen sources and methanol as a carbon source (Shen, et al., 1998). The FLD1 promoter can be induced with either methanol as a sole carbon source (and ammonium sulfate as a nitrogen source) or methylamine as a sole nitrogen source (and glucose as a carbon source). After induction with either methanol or methylamine, $P_{FLD1}$ is able to express levels of a β-lactamase reporter gene similar to those obtained with methanol induction from the AOX1 promoter. The FLD1 promoter offers the flexibility to induce high levels of expression using either methanol or methylamine, an inexpensive nontoxic nitrogen source.

d. The PEX8 and YPT1 Promoter

For some *P. pastoris* strains, the AOX1, GAP, and FLD1 promoters may be too strong, expressing genes at too high a level. There is evidence that, for certain foreign genes, the high level of expression from $P_{AOX1}$ may overwhelm the post-translational machinery of the cell, causing a significant proportion of foreign protein to be misfolded, unprocessed, or mislocalized (Thill, et al., 1990; Brierley, 1998). For these and other applications, moderately expressing promoters are desirable. Toward this end, the *P. pastoris* PEX8 and YPT1 promoters may be of use. The PEX8 gene encodes a peroxisomal matrix protein that is essential for peroxisome biogenesis (Liu, et al., 1995). It is expressed at a low but significant level on glucose and is induced modestly when cells are shifted to methanol. The YPT1 gene encodes a GTPase involved in secretion, and its promoter provides a low but constitutive level of expression in media containing either glucose, methanol, or mannitol as carbon sources (Sears, et al., 1998).

e. Alternative Promoters

Synthetic hybrid promoters consisting of the upstream activator sequence of one yeast promoter, which allows for inducible expression, and the transcription activation region of another yeast promoter also serve as functional promoters in a yeast host.

Yeast-recognized promoters also include naturally occurring non-yeast promoters that bind yeast RNA polymerase and initiate translation of the coding sequence. Such promoters are available in the art. See, for example, Cohen et al. (1980); Mercereau-Puigalon et al. (1980); Panthier et al. (1980); Henikoff et al. (1981); and Hollenberg et al. (1981), each of which is herein incorporated by reference.

ii. Signal Sequences and Leader Sequences

In addition to encoding the protein of interest, the expression cassette's chimeric gene may encode a signal peptide that allows processing and translocation of the hybrid IFN protein, as appropriate.

For purposes of the present invention, the signal peptide is a presequence that is an N-terminal sequence for the precursor polypeptide of the mature form of a yeast secreted protein. When the nucleotide sequence encoding the hybrid precursor polypeptide is expressed in a transformed yeast host cell, the signal peptide sequence functions to direct the hybrid precursor polypeptide comprising the mature heterologous protein of interest into the endoplasmic reticulum (ER). Movement into the lumen of the ER represents the initial step into the secretory pathway of the yeast host cell. The signal peptide of the invention can be heterologous or native to the yeast host cell. The signal peptide sequence of the invention may be a known naturally occurring signal sequence or any variant thereof as described above that does not adversely affect the function of the signal peptide.

During entry into the ER, the signal peptide is cleaved off the precursor polypeptide at a processing site. The processing site can comprise any peptide sequence that is recognized in vivo by a yeast proteolytic enzyme. This processing site may be the naturally occurring processing site for the signal peptide. More preferably, the naturally occurring processing site will be modified, or the processing site will be synthetically derived, so as to be a preferred processing site. By "preferred processing site" is intended a processing site that is cleaved in vivo by a yeast proteolytic enzyme more efficiently than is the naturally occurring site. Examples of preferred processing sites include, but are not limited to, dibasic peptides, particularly any combination of the two basic residues Lys and Arg, that is Lys-Lys, Lys-Arg, Arg-Lys, or Arg-Arg, most preferably Lys-Arg. These sites are cleaved by the endopeptidase encoded by the KEX2 gene of *P. pastoris* (Julius et al. (1983). In the event that the KEX2 endopeptidase would cleave a site within the peptide sequence for the mature heterologous protein of interest, other preferred processing sites could be utilized such that the peptide sequence of interest remains intact (see, for example, Sambrook et al. (1989)).

A functional signal peptide sequence is essential to bring about extracellular secretion of a heterologous protein from a yeast cell. Additionally, the hybrid precursor polypeptide may comprise a secretion leader peptide sequence of a yeast secreted protein to further facilitate this secretion process. When present, the leader peptide sequence is generally positioned immediately 3' to the signal peptide sequence processing site. By "secretion leader peptide sequence" is intended a peptide that directs movement of a precursor polypeptide, which for the purposes of this invention is the hybrid precursor polypeptide comprising the mature heterologous protein to be secreted, from the ER to the Golgi apparatus and from there to a secretory vesicle for secretion across the cell membrane into the cell wall area and/or the growth medium. The leader peptide sequence may be native or heterologous to the yeast host cell.

The leader peptide sequence of the present invention may be a naturally occurring sequence for the same yeast secreted protein that served as the source of the signal peptide sequence, a naturally occurring sequence for a different yeast secreted protein, or a synthetic sequence, or any variants thereof that do not adversely affect the function of the leader peptide.

a. *S. cerevisiae* α-factor Prepro Peptide

For purposes of the invention, the leader peptide sequence when present is preferably derived from the same yeast secreted protein that served as the source of the signal peptide sequence, more preferably an alpha-factor protein. A number of genes encoding precursor alpha-factor proteins have been cloned and their combined signal-leader peptide sequences identified. See, for example, Singh et al. (1983). Alpha-factor signal-leader peptide sequences have been used to express heterologous proteins in yeast. See, for example, Elliott et al. (1983); Bitter et al. (1984); and Smith et al. (1985).

Alpha-factor, an oligopeptide mating pheromone approximately 11 residues in length, is produced from a larger precursor polypeptide of between about 100 and 200 residues in length, more typically about 120–160 residues. This precursor (pre) polypeptide comprises the signal sequence, which is about 19–23 (more typically 20–22 residues), the leader sequence (pro), which is about 60–66 residues, and typically 2–6 tandem repeats of the mature pheromone sequence. Although the signal peptide sequence and full-length alpha-factor leader peptide sequence can be used, the invention also contemplates a truncated alpha-factor leader peptide sequence which can be used with the signal peptide when both elements are present in the hybrid precursor molecule.

The processing of this signal sequence involves three steps. The first is the removal of the pre signal by signal peptidase in the endoplasmic reticulum. Second, Kex2 endopeptidase cleaves between Arg-Lys of the pro leader sequence. This is rapidly followed by cleavage of Glu-Ala repeats, if present, by the Ste13 protein (Brake, et al, 1984).

When the hybrid precursor polypeptide sequence of the present invention comprises a leader peptide sequence, such as the alpha-factor leader sequence, there can be a processing site immediately adjacent to the 3' end of the leader peptide sequence. This processing site enables a proteolytic enzyme native to the yeast host cell to cleave the yeast secretion leader peptide sequence from the 5' end of the native N-terminal propeptide sequence of the mature heterologous protein of interest, when present, or from the 5' end of the peptide sequence for the mature heterologous hybrid IFN. The processing site can comprise any peptide sequence that is recognized in vivo by a yeast proteolytic enzyme such that the mature heterologous protein of interest can be processed correctly. The peptide sequence for this processing site may be a naturally occurring peptide sequence for the native processing site of the leader peptide sequence. More preferably, the naturally occurring processing site will be modified, or the processing site will be synthetically derived, so as to be a preferred processing site as described above.

b. Alternative Signal Sequences

Suitable signal sequences may also include *P. pastoris* Acid Phosphatase (PHO1) and PHA-E from the plant lectin *Phaseolus vulgaris* agglutinin (Cereghino and Cregg, 2000; and Raemaekers, et al., 1999). In addition, the signal sequence may be synthetically derived, or determined from genomic or cDNA libraries using hybridization probe techniques available in the art (see Sambrook et al. (1989).

In accordance with the invention as stated above, the yeast signal peptide and secretion leader peptide sequences represent those parts of the hybrid precursor polypeptide of the invention that can direct the sequence for the mature heterologous IFNαD through the secretory pathway of a yeast host cell.

iii. Hybrid IFN Peptide Coding Sequences

An exemplary hybrid IFN coding sequence is shown in Table 2 for the HVV molecule. The origin of the coding sequences is discussed in Example 1, and illustrated in FIGS. 1–4.

Where appropriate, the nucleotide sequence encoding the hybrid IFN peptides and any additional nucleotide sequences of interest may be optimized for increased expression in the transformed yeast. That is, these nucleotide sequences can be synthesized using yeast-preferred codons for improved expression. Methods are available in the art for synthesizing yeast-preferred nucleotide sequences of interest (see, for example, U.S. Pat. Nos. 5,219,759 and 5,602,034 which are expressly incorporated by reference herein in their entirety).

Additional sequence modifications are known to enhance expression of nucleotide coding sequences in yeast hosts. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the nucleotide coding sequence is modified to avoid predicted hairpin secondary mRNA structures.

iv. Transcription and Translation Terminators

The termination regulatory region of the expression cassette may be native with the transcription initiation region, or may be derived from another source, providing that it is recognized by the yeast host. The termination regions may be those of the native alpha-factor transcription termination sequence, or another yeast-recognized termination sequence, such as those for the enzymes mentioned above. The transcriptional termination region may be selected, particularly for stability of the mRNA, to enhance expression.

Preferably the transcription terminator is the Mat-alpha (alpha-factor) transcription terminator. More preferably the transcription termination sequence is the AOX1 transcription termination region as shown in FIG. 1.

v. Selectable Markers

Selectable markers include the biosynthetic pathway genes HIS4 from either *P. pastoris* or *S. cerevsiae,* ARG4 from *S. cerevisiae,* and the Sh ble gene from *Streptoalloteichus hindustanus* which confers resitance to the bleomycin-related drug Zeocin (Gregg et al., 1985; Gregg and Madden, 1989; and Higgins, et al., 1998). A more recently developed set of biosynthetic markers includes the *P. pastoris* ADE1 (PR-amidoimidazolesuccinocarboxamide synthase), ARG4 (argininosuccinate lyase), and URA3 (orotidine 5'-phosphate decarboxylase) genes.

vi. Construction of Transforming Vector

As is the case for the heterologous hybrid IFN proteins, each of the other elements present in the hybrid precursor polypeptide can be a known naturally occurring polypeptide sequence or can be synthetically derived, including any variants thereof that do not adversely affect the function of the element as described herein. By "adversely affect" is intended that inclusion of the variant form of the element results in decreased bioactivity of the secreted mature heterologous protein of interest relative to the hybrid precursor polypeptide comprising the native form of the element.

In preparing the expression cassette, the various nucleotide sequence fragments may be manipulated, so as to provide for the sequences in the proper orientation and, as appropriate, in the proper reading frame. Toward this end, adapters or linkers may be employed to join the nucleotide fragments or other manipulations may be involved to provide for convenient restriction sites, removal of superfluous nucleotides, removal of restriction sites, or the like. For this purpose, in vitro mutagenesis, primer repair, restriction, annealing, resubstitutions, e.g, transitions and transversions, may be involved. See particularly Sambrook et al. (1989).

The expression cassettes of the present invention can be ligated into a replicon (e.g., plasmid, cosmid, virus, minichromosome), thus forming an expression vector that is capable of autonomous DNA replication in vivo. Preferably the replicon will be a plasmid. Such a plasmid expression vector will be maintained in one or more replication systems, preferably two replications systems, that allow for stable maintenance within a prokaryotic host for cloning purposes and integration within a yeast host cell for expression purposes.

Additionally, a plasmid expression vector may be integrated as a high or low copy number plasmid. A strain that contains multiple integrated copies of an expression cassette can sometimes yield more heterologous protein than single copy strains (Clare, et al., 1991).

B. Transformation of Yeast Cells

Yeast cells are transformed with expression constructs described above using a variety of standard techniques including, but not limited to, electroporation, microparticle bombardment, spheroplast generation methods, or whole cell methods such as those involving lithium chloride and polyethylene glycol (Cregg et al., 1985; Liu et al., 1992; Waterham et al., 1996; and Cregg and Russell, 1998).

C. Culturing and Obtaining Secreted Hybrid IFN Proteins

Transformants are grown in an appropriate nutrient medium, and, where appropriate, maintained under selective pressure to insure retention of endogenous DNA. Where expression is inducible, growth can be permitted of the yeast host to yield a high density of cells, and then expression is induced. The recombinant production of an exemplary hybrid IFN protein, HVV, is described in Example 2. Partial purification of HVV is described in Example 3.

In accordance with an important aspect of this invention, it has been found that the transformed *P. pastoris* is able to express and secrete hybrid IFN proteins having a specific activity of between about $2.75 \times 10^8$ U/mg to about $3 \times 10^8$ U/mg as disclosed in Example 4. The determination of specific activity can be performed by antiviral assays which are known to those skilled in the art. An exemplary antiviral assay is described in Example 5. Another antiviral assay is described in Pontzer and Johnson, 1985, which is hereby incorporated by reference in its entirety.

D. Isolating Secreted Human IFNαD

One of the major advantages of expressing rHuIFNαD as a secreted protein in *Pichia pastoris* is that *Pichia* secretes very low levels of contaminating native proteins in the culture medium. That, combined with the use of the minimal *Pichia* growth medium with low protein content, led to the efficient secretion of a biologically active rHuIFNαD that constitutes the vast majority of the total protein in the medium.

In essence, the very nature of this secreted expression system allows for simply the secretion of the protein into the medium to serve as the first step in the purification process. This results in a straightforward and simple procedure for further purification using techniques such as molecular sieve and ion-exchange chromatography, electrophoresis, dialysis, solvent-solvent extraction, and the like. Such methods are known in the art and described for example in Deutscher, 1990 and Scopes, 1982.

Figure 8:
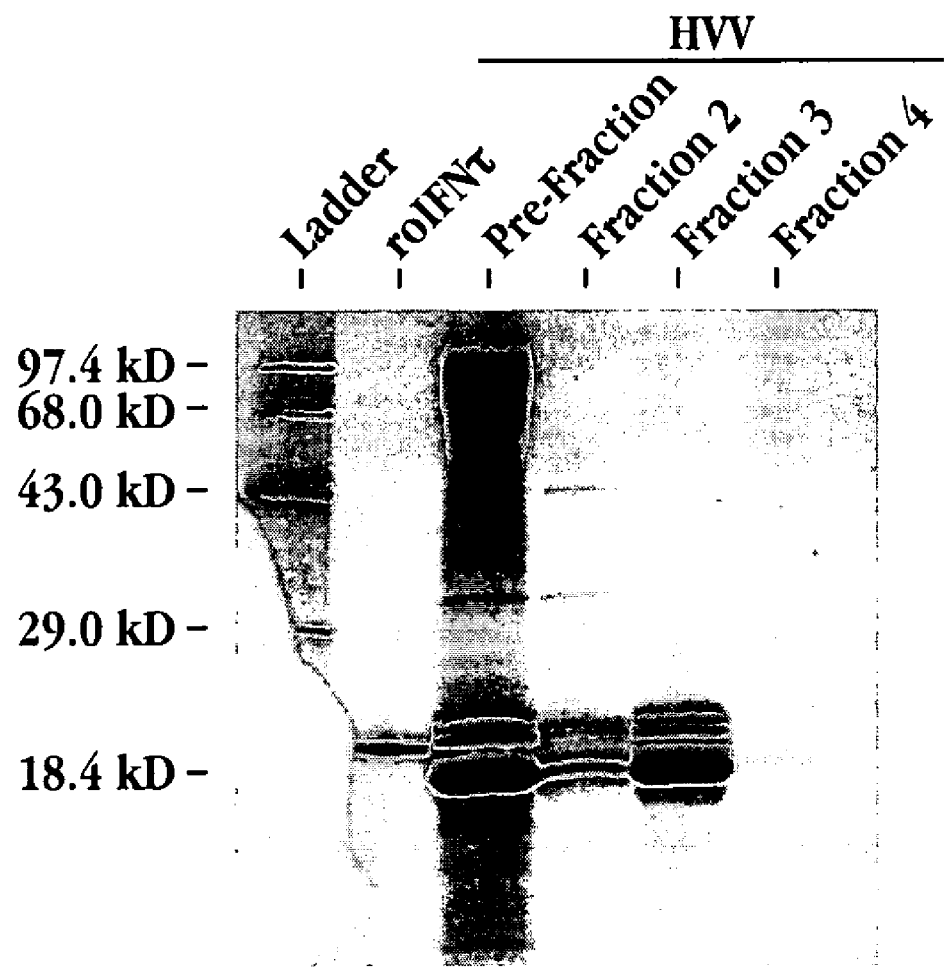

As described in Example 3, one round of molecular sieve chromatography essentially eliminated the higher molecular weight contaminating proteins leaving behind a very pure hybrid IFN (FIG. 8) with a very high antiviral activity.

IV. Applications

The hybrid IFN proteins of the present invention find utility in treating a variety of cancers and viral diseases including those for which other interferons have previously shown activity. See, for example, U.S. Pat. Nos. 4,885,166, 4,975,276, and 5,939,286, each of which is expressly incorporated by reference in their entirety. One exemplary viral illness for which the present invention contemplates a treatment is hepatitis C virus (HCV).

HCV is a major public health problem affecting an estimated 170 million people worldwide and more than 10% of the population in some countries (Lechner, et al., 2000). HCV is transmitted primarily by transfusion of infected blood and blood products (Cuthbert, et al., 1994; Mansell, et al., 1995). The Centers for Disease Control and Prevention estimate that HCV is responsible for 160,000 new cases of acute hepatitis in the United States each year. Therefore, an urgent medical need exists for an effective anti-HCV agent.

HCV is a positive-stranded, lipid-enveloped RNA virus of the Flaviviridae family, approximately ten thousand nucleotides in length (Choo, et al., 1989). HCV, unlike hepatitis B virus, has no DNA intermediate, and therefore cannot be integrated into the host genome (Berenguer, et al., 1996). Although HCV has been cloned, the virus has been difficult to culture in vitro (Trepo, 2000). HCV is extremely persistent, producing a chronic infection in 85% of infected individuals, although the mechanism of this persistence is unknown (Trepo, 2000).

Treatment of HCV is aimed at reducing inflammation and liver cell damage, thus preventing cirrhosis and hepatocellular carcinoma (Horiike, et al., 1998; Benvegnu, et al., 1998). Therapies that are currently available for HCV are only effective for a small subpopulation of infected patients (Magrin, et al., 1994; Choo, et al., 1991; Choo, et al., 1989). IFN-α was introduced as therapy for chronic hepatitis C in the United States in 1991 and in Japan in 1992 (Saito, et al., 2000). However, as described above, use of IFN-α in sufficient dosage to yield clinical efficacy (i.e., at amounts of about $1 \times 10^6$ units/treatment and above) is usually associated with a number of sever side effects.

The lower cytotoxicity of the hybrid proteins of the present invention positions them as attractive candidates for illnesses such as HCV.

V. Pharmaceutical Compostions

Hybrid interferon fusion proteins of the present invention can be formulated according to known methods for preparing pharmaceutically useful compositions. Formulations comprising interferons or interferon-like compounds have been previously described. In general, the compositions of the subject invention will be formulated such that an effective amount of the hybrid interferon is combined with a suitable carrier in order to facilitate effective administration of the composition.

The compositions used in these therapies may also be in a variety of forms. These include, for example, solid, semi-solid, and liquid dosage forms, such as tablets, pills, powders, liquid solutions or suspensions, liposomes, suppositories, injectable, and infusible solutions. The preferred form depends on the intended mode of administration and therapeutic application. The compositions also preferably include conventional pharmaceutically acceptable carriers and adjuvants which are known to those of skill in the art. Preferably, the compositions of the invention are in the form of a unit dose and will usually be administered to the patient one or more times a day.

Hybrid interferon fusion polypeptides or related polypeptides, may be administered to a patient in any pharmaceutically acceptable dosage form, including oral intake, inhalation, intranasal spray, intraperitoneal, intravenous, intramuscular, intralesional, or subcutaneous injection. Specifically, compositions and methods used for other interferon compounds can be used for the delivery of these compounds.

One primary advantage of the compounds of the subject invention, however, is the extremely low cytotoxicity of the hybrid IFN proteins of the invention. Because of this low cytotoxicity, it is possible to administer the hybrid interferon compositions in concentrations which are greater than those which can generally be utilized for other interferon (e.g., IFN alpha) compounds. Thus, it is contemplated that hybrid interferon compositions of the present invention can be administered at rates from about $5\times10^4$ to $2\times10^7$ units/day to about $5\times10^7$ units/day or, preferably, to about $1\times10^8$ units/day, or even more preferably, to about $1\times10^{10}$ units/day. In another embodiment, the hybrid interferon compositions of the present invention are administered at dosages of to about $5\times10^{11}$ units/day, or preferably to about $5\times10^{12}$ units/day.

High doses are preferred for systemic administration. It should, of course, be understood that the compositions and methods of this invention may be used in combination with other therapies, for example ribavirin.

Ribavirin (1-β-D-ribofuranosyl-1,2,4-triazole-3-carboxamide) is a purine nucleoside analogue that has been found to interfere with viral mRNA synthesis and to inhibit in vivo and in vitro replication of a wide range of RNA and DNA viruses (Fernandez, et al., 1986; Balzarini, et al., 1991). Ribavirin has been shown to be efficient in normalizing aminotransferase levels, but has minor activity on serum HCV RNA titres in chronic hepatitis C patients (Di Bisceglie, et al., 1992). Even the beneficial effects of ribavirin, however, are transient (Clarke, 2000; Koskinas, et al., 1995), and because of severe side effects, ribavirin, in combination with IFN-α, can be difficult to tolerate (Cotler, et al., 2000). Thus, ribivirin, in combination with the hybrid IFN proteins of the present invention may be preferably to ribivirin in combination with native IFN-α.

Once improvement of a patient's condition has occurred, a maintenance dose is administered if necessary. Subsequently, the dosage or the frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

From the foregoing, it can be seen how various objects and features of the invention are met.

| Description | SEQ. ID NO. |
|---|---|
| HVV Amino Acid Sequence<br>CDLPETHSLDNRRTLMLLAQMSRISPSSCLMDRHDFGFPQEEFD<br>GNQFQKAPAISVLHELIQQIFNLFTTKDSSAAWDEDLLDKFCTE<br>LYQQLNDLEACVMQEERVGETPLMNADSILAVKKYFRRITLYLT<br>EKKYSPCAWEVVRAEIMRSLSLSTNLQERLTKMGGDLNSP | 1 |
| HVV Nucleotide Sequence<br>TGTGATTTGCCAGAGACTCACTCTTTGGACAACAGAAGAACTTT<br>GATGCTTTTGGCCCAAATGTCTAGAATCTCTCCATCCTCTTGTT<br>TGATGGATAGACACGATTTCGGTTTCCCACAAGAAGAATTTGAC<br>GGTAACCAATTCCAAAAGGCTCCTGCTATTTCTGTTTTGCACGA<br>GTTGATTCAACAAATTTTCAACTTGTTCACCACTAAGGACTCTT<br>CTGCTGCCTGGGACGAAGACTTGTTGGACAAGTTCTGTACTGAG<br>CTTTACCAACAATTGAACGACTTGGAGGCTTGTGTTATGCAAGA<br>GGAGAGAGTCGGTGAGACCCCATTGATGAACGCTGATTCCATCT<br>TGGCTGTCAAGAAGTACTTCAGAAGAATTACCTTGTACTTGACC<br>GAAAAGAAGTACTCCCCATGTGCCTGGGAAGTCGTTAGAGCCGA<br>AATCATGAGATCTTTGTCCTTGTCCACTAACTTGCAAGAGAGAC<br>TTACCAAGATGGGTGGAGACTTGAACTCTCCATAA | 2 |

VII. EXAMPLES

The following examples further illustrate the invention described herein and are in no way intended to limit the scope of the invention.

Example 1

HVV Cloning Strategy

The HVV molecule is a hybrid molecule consisting of the HuIFNαD molecule with the four final amino acids from the C-terminus (residues 163–166 of SEQ ID NO:57) replaced with the ten final C-terminal end amino acids from ovine IFN-τ (residues 163–172 of SEQ ID NO:55). The resulting amino acid coding sequence was used to generate a corresponding DNA coding sequence with codon usage optimized for expression in *Pichia pastoris*. The DNA coding sequence was synthetically constructed by sequential cloning of oligonucleotide fragments (approximately 150 base pairs in length; FIGS. 1–4) into a bacterial vector called G2 (Operon Technologies, Alameda, Calif.). Each of the four 150 base pair fragments (HVV Fragments 1–4) were created by ligation of overlapping synthetic oligonucleotides (<40 bp in length) designed with specific restriction enzyme 5' or 3' overhangs to simplify cloning into the vector.

| | |
|---|---|
| A. Cloning step #1 | |
| Vector to cut: | G2 |
| Cut with enzymes: | XbaI and BamHI |
| Fragment to ligate: | Fragment 1 (FIG. 1) |
| New vector name: | G2HVV1F1 |
| B. Cloning step #2 | |
| Vector to cut: | G2HVV1F1 |
| Cut with enzymes: | EcoRI and BamHI |
| Fragment to ligate: | Fragment 2 (FIG. 2) |
| New vector name: | G2HVV1F2 |
| C. Cloning step #3 | |
| Vector to cut: | G2HVV1F2 |
| Cut with enzymes: | Sac I and BamHI |
| Fragment to ligate: | Fragment 3 (FIG. 3) |
| New vector name: | G2HVV1F3 |
| D. Cloning step #4 | |
| Vector to cut: | G2HVV1F3 |
| Cut with enzymes: | EcoRI and BamHI |
| Fragment to ligate: | Fragment 4 (FIG. 4) |
| New vector name: | G2HVV1F4 |
| E. Final Check | |
| Cut with enzyme: | Sac II |

The HVV gene was cut out of G2HVV1F4 vector and ligated into the pPICZ-α□vector (Invitrogen, San Diego) using the XhoI and NotI sites on the plasmid. The sequence of the HVV-pPICZ-α construct is depicted in FIGS. 5A-5.

Example 2

Recombinant Production of HVV in *P. pastoris*

Selected positive *P. pastoris* HVV transformants were grown overnight in BMGY medium, and then the cells were induced using an $OD_{600}$ of 2 in BMMY methanol-containing medium. The cultures were fed with 1 ml of 10% methanol at 24 and 48 hours post-induction. After 72 hours of culture, the entire culture supernatant was harvested, filter sterilized and analyzed by 14% Tris-glycine SDS-PAGE stained with Colloidal Coomassie (Novex, San Diego, Calif.). Supernatant from a pPICZα control plasmid transformant was used as the negative control. The results, as shown in FIG. 7, reveal that clone HVV-16 yielded the strongest HVV expression.

Example 3

HVV Purification

FIG. 8 illustrates the partial purifcation of HVV protein from *P. pastoris* supernatants. Culture supernatants (20 ml volume) were buffer exchanged with 10 mM Tris, 150 mM NaCl and concentrated to a final volume of 2 ml (Pre-fraction) prior to loading onto a HiPrep Sephacryl 26/60 S-100 size-exclusion column. The first 120 ml flowthrough following the injection of the sample were collected at 1 ml/min and designated fraction 1. Three fractions of 20 ml each were collected and designated fractions 2, 3, and 4 respectively. Fractions 2, 3 and 4 were concentrated to 1 ml and run on 14% SDS-PAGE gel and stained with Novex colloidal blue staining kit.

Example 4

HVV Antiviral Specific Activity

HVV protein was partially purified as described in Example 3 from HVV clone 16 (FIG. 7), *P. pastoris* recombinant culture supernatants using size-exclusion gel chromatography. Fraction 3 (FIG. 8) from four different purification experiments (Sample IDs: S-0018; S-0019; S-0063; and S-0064) were each concentrated to 1 ml and total protein concentration and antiviral activity of each sample were determined as described in Example 5 below. The results are shown in Table 3 below.

TABLE 3

HVV-16 Antiviral Specific Activity

| SAMPLE ID | PROTEIN CONCENTRATION (MG/ML) | ANTIVIRAL UNITS (AVU/ML) | ANTIVIRAL SPECIFIC ACTIVITY (AVU/MG) | AVGERAGE AVU/MG ± STD (N) |
|---|---|---|---|---|
| S-0018 | 0.751 | $2.22 \times 10^8$ | $2.96 \times 10^8$ | $2.86 \times 10^8 \pm 0.09$ |
| S-0019 | 0.696 | $1.92 \times 10^8$ | $2.76 \times 10^8$ | (N = 4) |
| S-0063 | 1.102 | $3.11 \times 10^8$ | $2.82 \times 10^8$ | |
| S-0064 | 1.422 | $4.10 \times 10^8$ | $2.88 \times 10^8$ | |

Example 5

Quantitative Antiviral Assay

Madin Darby bovine kidney (MDBK) cells are grown to confluency in 96-well flat bottom plates using Eagle's MEM supplemented with 10% fetal bovine serum (FBS) and antibiotics. Once the cells are confluent, the assay medium is Eagle's MEM supplemented with 2% FBS and antibiotics. The challenge virus preparation of VSV is tested in a preliminary logarithmic serial dilution to determine an optimum working dilution that will give 100% CPE of the confluent MDBK cells after overnight incubation of virus alone (i.e. 16–24 hours). The VSV dilution ranges from $10^{-1}$ to $10^{-6}$ per 50 μl/well using four replicate wells per dilution with a final total volume of 200 μl/well in a 96-well plate. Based upon the dilution of the virus that creates 100% CPE, the $TCID_{50}$ is determined. At present, the stock virus being used has $10^{65}$ $TCID_{50}$/ml. The actual number of infectious virus particles being used in the assay is $10^{35}$ $TCID_{50}$/well.

To test the interferons, the MDBK cells are grown to confluency before the growth medium is removed and the cells are washed once with sterile PBS. Medium with interferon samples or without interferon as controls is then added in triplicate using serial 10-fold dilutions (e.g. $10^{-1}$ to $10^{-10}$) at 100 μl/well using the assay medium described above. The cells are then incubated for 18 hours at 37° C. Recombinant HuIFNαA (Biosource Intl., Camarillo, Calif.) can be used as the standard interferon control. After the interferon incubation step, cells are washed twice with PBS prior to addition of 100 μl per well of the predetermined virus dilution @ $10^{35}$ $TCID_{50}$/well. The virus is added to both the interferon treated test wells and non-treated wells and incubated for an additional 16–24 hours at 37° C. 100 μl of medium will then be removed from each well and replaced with 100 μl of 0.2% neutral red solution (Gibco-BRL) and incubated for 1 hour at 37° C. All media is removed and cells are gently washed twice with PBS before addition of 100 μl of acid alcohol (50% ethanol, 1% acetic acid). The $A_{550}$ of solubilized dye is read with a Bio-Kinetics Reader (Bio-Tek Instruments, Winooski Vt.). Percent protection is calculated using the following formula:

$$\text{Percent Protection} = \frac{[AVG(A_{550}\text{ Test Well}) - AVG(A_{550}\text{ Virus Control Well})]}{[AVG(A_{550}\text{ Untreated Cell Control Wells})]} \times 100$$

1 antiviral unit (U) is defined as 50% protection. The interferon titer (units/ml) will be read as the reciprocal of the dilution (per 0.1 ml of the sample) representing 50% protection of the cell monolayer, multiplied by a factor of 10.

Once the antiviral units/ml of the interferon is determined using the 10-fold dilution range, this data is used to determine the starting dilution for a two-fold dilution range (maximum of 10 dilutions) of the interferon in the assay. This gives a more exact antiviral units/ml value for the interferon being tested. Note that this colorimetric assay is an adaptation of the assay published by Crawford-Miksza et al. (1994).

Example 6

In Vitro Toxicity Assays Testing IFNα Analogs in Peripheral Blood Mononuclear Cells The in vitro toxicity of HuIFNα, OvIFNτ, and the IFN hybrid proteins were compared using peripheral blood mononuclear cells (PBMC). The buffy coat fraction of whole blood was diluted 1:4 with PBS and overlayed onto Nycoprep 1.077 (Nycomed Pharma, Oslo, Norway). After centrifugation at 600×g for 20 minutes at 20° C., the PBMC, which band at the interface, was removed using a pipette. The cells were then washed once with PBS and plated at a concentration of $5 \times 10^5$ cells/well in a 96-well plate. After plating, the cells were treated with 2000 U/ml to 128,000 U/ml of IFNα, IFNτ, or the IFN hybrid proteins in triplicate. After twelve days of incubation, the cells were ready to be assayed using the Annexin V Assay (Pharmingen). Note that these assays are routinely used in our laboratories and have given us consistent, reliable quantitative results.

Annexin V Assay:

Annexin V is a 35–36 kD $Ca^{2+}$ dependent, phospholipid binding protein that has high affinity for phospholipid phosphatidylserine (PS). In apoptotic cells, the membrane PS is translocated from the inner to the outer leaflet of the plasma membrane. Annexin V binds cells that are undergoing the early stages of apoptosis with exposed membrane PS. Therefore, staining with Annexin V in conjunction with propidium iodide, a vital dye, allows the identification of early apoptotic cells. This assay does not distinguish between cells that have already undergone apoptosis and those cells that have died as a result of necrosis.

The PBMC's are harvested from 3 wells and prepared for the Annexin V Assay as specified by the Pharmingen Assay manual. The Annexin V Assay Kit comes with all the reagents required for cell staining. The stained cells were acquired and analyzed using the Becton Dickinson FACScan and the CellQuest Software. It is important to note that there is a basal level of apoptosis (Annexin V positive, propidium iodide negative) and necrosis (Annexin V and propidium iodide double positive) within the PBMC population, and this level is slightly different for each donor. Thus, the untreated population is used to define the basal level of apoptotic and dead cells. Data for each sample were presented as Percent Specific Cell Death (Annexin V+ or Propidium Iodide+) from a total of 10,000 cells acquired using the following formula:

$$\% \text{ Specific Cell Death} = \frac{(\%\text{ Annexin V * positive cells from untreated wells})}{(\%\text{ AnnexinV positive cells from treated wells})} \times 100$$

*Note:
When calculating % Specific Cell Death based on propidium iodide staining, replace Annexin V values with propidium iodide values.

Example 7

Human PBMC ($5 \times 10^5$/well) were incubated with either rHuIFNα or roIFNα at $1.5 \times 10^5$ antiviral U/ml for 12 days then double-stained with AnnexinV-FITC and propidium iodide. Percent specific cell death was calculated by using the following formula: [(%AV+ or PI+ cells from control wells)/(% AV+ or PI+ cells from treated wells)×100].

TABLE 4

Percent Specific Cell Death Based Upon Annexin V Positive Cells

|  | HVV-16 | rHuIFNαD (Biosource) | rHuIFNαD (Pepgen) | BSA Control |
|---|---|---|---|---|
| AVG ± STD | 12.88 ± 15.44 | 65.00 ± 22.49 | 45.46 ± 23.64 | 7.67 ± 14.57 |
| MEDIAN | 4.88 | 65.78 | 43.95 | 0.00 |
| N | 6 | 10 | 10 | 10 |

TABLE 5

Percent Specific Cell Death Based Upon Propidium Iodide Positive Cells

|  | HVV-16 | rHuIFNαD (Biosource) | rHuIFNαD (Pepgen) | BSA Control |
|---|---|---|---|---|
| AVG ± STD | 2.08 ± 3.85 | 32.88 ± 15.69 | 19.32 ± 12.55 | 3.78 ± 8.19 |
| MEDIAN | 0.56 | 34.59 | 15.27 | 0.00 |
| N | 6 | 10 | 9 | 10 |

Example 8

Percent Specific Cell Death Analyzed by Flow Cytometry

Figure 9:
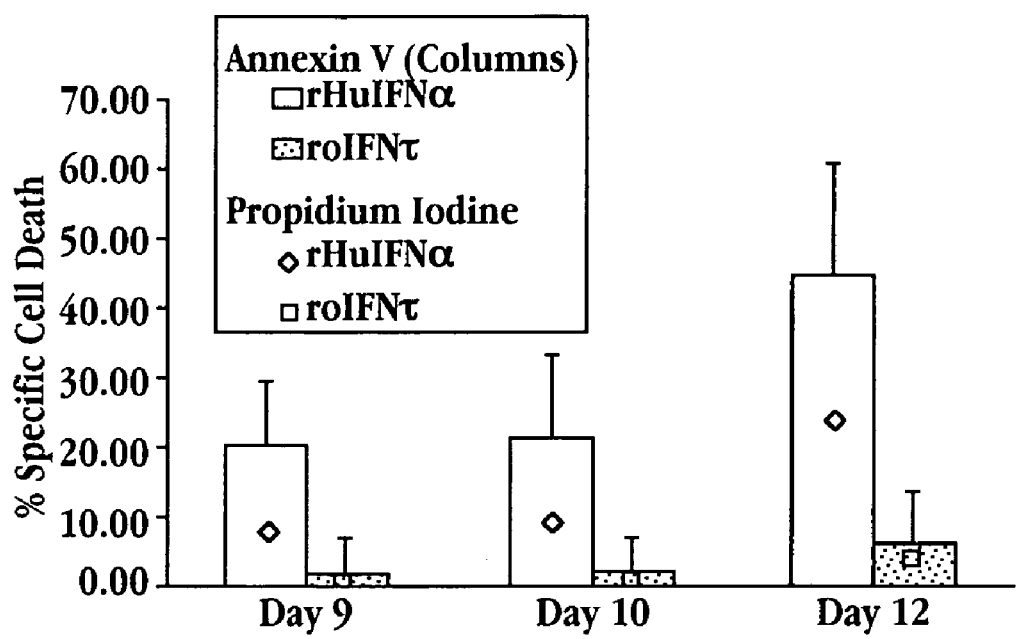

FIG. 9 shows the percent specific cell death as analyzed by flow cytometry. Human PBMC ($5 \times 10^5$/well) were incubated with either rHuIFNα or roIFNτ at $1.5 \times 10^5$ antiviral U/ml for 9, 10, and 12 days then double-stained with AnnexinV-FITC and propidium iodide. Percent specific cell death was calculated by using the following formula: [(% AV+ or PI+ cells from control wells)/(% AV+ or PI+ cells from treated wells)×100]. Columns and symbols show Annexin V and propidium iodide calculations, respectively.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the invention has been described with respect to particular embodiments, it will be apparent to those skilled in the art that various changes and modifications can be made without departing from the invention.

It is claimed:

1. An interferon-α/interferon-τ hybrid protein comprising:
   about 172 amino acid residues having an N-terminal region and a C-terminal region; wherein,
   the N-terminal region is selected from a group consisting of (i) a sequence of amino acid residues ranging from about position 1 to about position 162 of human interferon-αD (SEQ ID NO:57), and (ii) any amino acid sequence having at least 95% homology to the residues ranging from about position 1 to about position 162 of SEQ ID NO:57;
   the C-terminal region is selected from a group consisting of a sequence of amino acid residues ranging from about position 163 to about position 172 of (i) a ruminant interferon-τ (SEQ ID NO:55 or SEQ ID NO:56), and (ii) any amino acid sequence having at least 95% homology to the residues ranging from about position 163 to about position 172 of SEQ ID NO:55 or SEQ NO:56;
   and wherein, the hybrid protein has at least one function of human interferon-αD and a reduced cytotoxicity relative to the cytoxicity of the human interferon-αD.

2. The hybrid protein of claim 1, wherein the ruminant interferon-τ consists of an ovine or bovine interferon-τ.

3. The hybrid protein of claim 1 consisting of SEQ ID NO:1.

4. The hybrid protein of claim 1 having an antiviral function.

5. The hybrid protein of claim 1, wherein the hybrid protein is pegylated.

6. A composition comprising the hybrid protein of claim 1.

7. The composition of claim 6 comprising SEQ ID NO: 1.

8. The composition of claim 6 further comprising ribavirin.

* * * * *